US011027021B2

(12) United States Patent
Arthur et al.

(10) Patent No.: US 11,027,021 B2
(45) Date of Patent: Jun. 8, 2021

(54) COMBINATIONS OF PBD-BASED ANTIBODY DRUG CONJUGATES WITH BCL-2 INHIBITORS

(71) Applicant: Seagen Inc., Bothell, WA (US)

(72) Inventors: William Arthur, Bainbridge Island, WA (US); Robert Thurman, Kenmore, WA (US); Travis Biechele, Seattle, WA (US); Rory Rohm, Monroe, WA (US)

(73) Assignee: Seagen Inc., Bothell, WA (US)

( * ) Notice: Subject to any disclaimer, the term of this patent is extended or adjusted under 35 U.S.C. 154(b) by 0 days.

(21) Appl. No.: 16/085,460

(22) PCT Filed: Mar. 15, 2017

(86) PCT No.: PCT/US2017/022472
§ 371 (c)(1),
(2) Date: Sep. 14, 2018

(87) PCT Pub. No.: WO2017/160954
PCT Pub. Date: Sep. 21, 2017

(65) Prior Publication Data
US 2019/0076549 A1    Mar. 14, 2019

Related U.S. Application Data

(60) Provisional application No. 62/308,778, filed on Mar. 15, 2016, provisional application No. 62/356,814, (Continued)

(51) Int. Cl.
*A61K 47/68* (2017.01)
*C07K 16/28* (2006.01)
(Continued)

(52) U.S. Cl.
CPC .... *A61K 47/6867* (2017.08); *A61K 39/39558* (2013.01); *A61K 47/6803* (2017.08);
(Continued)

(58) Field of Classification Search
None
See application file for complete search history.

(56) References Cited

U.S. PATENT DOCUMENTS 6,248,516 B1   6/2001  Winter et al.
7,419,811 B2   9/2008  Lavie et al.
(Continued)

FOREIGN PATENT DOCUMENTS

CA   2733223 A1   2/2010
EP   2625201 B1   9/2016
(Continued)

OTHER PUBLICATIONS

Gerber et al. ("Gerber" Blood, 2009, 113, 4352-4361). (Year: 2009).*
(Continued)

*Primary Examiner* — Karl J Puttlitz
(74) *Attorney, Agent, or Firm* — Seagen Inc.

(57) ABSTRACT

This invention relates to treatment of cancer using antibody drug conjugates that comprise PBD molecules in combination with Bcl-2 inhibitors.

11 Claims, 10 Drawing Sheets

Specification includes a Sequence Listing.

Related U.S. Application Data filed on Jun. 30, 2016, provisional application No. 62/428,770, filed on Dec. 1, 2016.

(51) Int. Cl.

| | |
|---|---|
| *A61K 39/395* | (2006.01) |
| *A61P 35/02* | (2006.01) |
| *C07K 16/32* | (2006.01) |

(52) U.S. Cl.
CPC .......... *A61K 47/6849* (2017.08); *A61P 35/02* (2018.01); *C07K 16/2803* (2013.01); *C07K 16/2875* (2013.01); *C07K 16/2884* (2013.01); *C07K 16/32* (2013.01); *C07K 2317/24* (2013.01)

(56) References Cited

U.S. PATENT DOCUMENTS

| | | |
|---|---|---|
| 7,695,716 B2 | 4/2010 | Drachman et al. |
| 8,337,855 B2 | 12/2012 | Hoffee et al. |
| 8,455,622 B2 | 6/2013 | McDonagh et al. |
| 9,061,074 B2 | 6/2015 | Carter et al. |
| 9,079,958 B2 | 7/2015 | Konopitzkly et al. |
| 9,352,006 B2 | 5/2016 | Chen |
| 9,550,833 B2 | 1/2017 | Konopitzky et al. |
| 9,587,019 B2 | 3/2017 | Sutherland et al. |
| 2002/0022031 A1 | 2/2002 | Goldenberg et al. |
| 2004/0152632 A1 | 8/2004 | Feingold |
| 2007/0190060 A1 | 8/2007 | Boghaert et al. |
| 2008/0104734 A1 | 5/2008 | Kay et al. |
| 2010/0158909 A1 | 6/2010 | McDonagh et al. |
| 2010/0278779 A1 | 11/2010 | Zeldis |
| 2010/0305122 A1 | 12/2010 | Bruncko et al. |
| 2011/0159085 A1* | 6/2011 | Tong .................... A61K 9/4858 424/452 |
| 2011/0206700 A1 | 8/2011 | Hoffee et al. |
| 2011/0300139 A1 | 12/2011 | Kumar et al. |
| 2012/0082670 A1 | 4/2012 | Konopitzky et al. |
| 2012/0251554 A1 | 10/2012 | Bachmann et al. |
| 2013/0024177 A1 | 1/2013 | Nolan |
| 2013/0028919 A1 | 1/2013 | Howard et al. |
| 2013/0058919 A1 | 3/2013 | Lazar et al. |
| 2013/0109644 A1 | 5/2013 | MacBeth et al. |
| 2013/0309223 A1 | 11/2013 | Sutherland et al. |
| 2014/0011215 A1 | 1/2014 | Albitar et al. |
| 2014/0086942 A1 | 3/2014 | Carter et al. |
| 2014/0107119 A1 | 4/2014 | Bruncko et al. |
| 2014/0335549 A1 | 11/2014 | Albitar et al. |
| 2015/0125447 A1 | 5/2015 | Heider |
| 2015/0147316 A1* | 5/2015 | Sutherland ......... C07K 16/2803 424/133.1 |
| 2015/0320755 A1* | 11/2015 | Kutok ................ A61K 31/5377 514/235.8 |
| 2016/0046711 A1 | 2/2016 | Bialucha et al. |
| 2017/0204180 A1 | 7/2017 | Sutherland et al. |
| 2018/0169261 A1* | 6/2018 | Sutherland ......... A61K 31/5513 |
| 2019/0117787 A1 | 4/2019 | Kennedy et al. |
| 2019/0134215 A1 | 5/2019 | Kennedy et al. |
| 2019/0262354 A1 | 8/2019 | Arthur et al. |

FOREIGN PATENT DOCUMENTS

| | | |
|---|---|---|
| WO | WO2004/043344 A2 | 5/2004 |
| WO | WO2004/043461 A1 | 5/2004 |
| WO | WO2006/113909 A2 | 10/2006 |
| WO | WO2008/070593 A2 | 6/2008 |
| WO | WO2008/070593 A3 | 6/2008 |
| WO | WO2009/052431 A2 | 4/2009 |
| WO | WO2009/155386 A1 | 12/2009 |
| WO | WO2010/138588 A2 | 12/2010 |
| WO | WO2011/106389 A1 | 9/2011 |
| WO | WO2011/130613 A1 | 10/2011 |
| WO | WO2012/045752 A1 | 4/2012 |
| WO | WO2013/173496 A2 | 11/2013 |
| WO | WO2014/165119 A1 | 10/2014 |
| WO | WO2015/067570 A2 | 5/2015 |
| WO | WO2015/067570 A3 | 5/2015 |
| WO | WO2017/160954 A1 | 9/2017 |
| WO | WO2017/180768 A1 | 10/2017 |
| WO | WO2017/210621 A1 | 12/2017 |
| WO | WO2017/214433 A1 | 12/2017 |

OTHER PUBLICATIONS

FitzGerald et al. ("FitzGerald", Cancer Res, 2011, 7, 6300-6309) (Year: 2011).*
Almagro, et al., "Humanization of antibodies", Frontiers in Bioscience 13, pp. 1619-1633, (Jan. 1, 2008).
Amster, et al., "Synthesis of part of a monse immunoglobulin light chain in a bacterial clone", Nucleic Acids Research, vol. 8, No. 9, 2055-2066, (1980).
Atwell, et al., "Design and Expression of a Stable Bispecific Scfv Dimer With Affinity for both Glycophorin and N9 Neuraminidase", Molecular Immunology, vol. 33, No. 17, 1301-1312, (1996).
Balaian, et al., "5-Azacytidine Augments the Cytotoxicity of Mylotarg toward AML Blasts in Vitro and in Vivo", Blood, 110(11), 1835, (Nov. 2007).
Barthelemy, et al., "Comprehensive Analysis of the Factors Contributing to the Stability and Solubility of Autonomous Human $V_H$ Domains", the Journal of Biological Chemistry, vol. 283, No. 6, pp. 3639-3654, (Feb. 8, 2008).
Beiboer, et al., "Guided Selection of a Pan Carcinoma Specific Antibody Reveals Similar Binding Characteristics yet Structural Divergence Between the Original Murine Antibody and its Human Equivalent", J. Mol. Biol. 296, pp. 833-849, (2000).
Biddle-Snead, et al., "Assessment of myeloblast CD33 receptor occupancy (RO) by vadastuximab talirine in patients with acute myeloid leukemia (AML) receiving monotherapy treatment", Cancer Research. Proceedings: AACR Annual Meeting 2017, 77(13 supplement), Abstract CT120, (2017).
Bixby, et al., "Vadastuximab Talirine Monotherapy in Older Patients with Treatment Naive CD33-Positive Acute Myeloid Leukemia (AML)", Blood, 128(22):590, (2016).
Bose, et al., "Rational Design of a Highly Efficient Irreversible DNA Interstrand Cross-Linking Agent Based on the Pyrrolobenzodiazepine Ring System", J. Am. Chem. Soc. 114, 4939-4941, (1992).
Boss et al., "Assembly of functional antibodies from immunoglobulin heavy and light chains synthesised in *E. coli*", Nucleic Acids Research, vol. 12, No. 9, 3791-3806, (1984).
Bothwell, et al., "Somatic variants of murine immunoglobulin a light chains", Nature, vol. 298, No. 22, 380-382, (1982).
Breiner, et al., "Somatic DNA rearrangement generates functional rat immunoglobulin k chain genes: The Jk gene cluster is longer in rat than in mouse", Gene 18, 165-174, (1982).
Carter, et al., "Engineering antibodies for imaging and therapy", Current Opinion in Biotechnology 8, 449-454, (1997).
Casset, et al., "A peptide mimetic of an anti-CD4 monoclonal antibody by rational design", Biochemical and Biophysical Research Communications, 307:198-205, (2003).
Chaudri, et al., "Dual specificity antibodies using a double-stranded oligonucleotide bridge", FEBS Letters 450, 23-26, (1999).
Chen, et al., "Selection and Analysis of an Optimized Anti-VEGF Antibody: Crystal Structure of an Affinity-matured Fab in Complex with Antigen", J. Mol. Biol., 293:865-881, (1991).
Chipuk, et al., "Mitochondrial outer membrane permeabilization during apoptosis: the innocent bystander scenario", Cell Death and Differentiation 13, 1396-1402, (2006).
Choi, et al., "Predicting antibody complementarity determining region structures without classification", Mol. BioSyst., 7, pp. 3327-3334, (2011).
Chothia, et al., "Canonical Structures for the Hypervariable Regions of Immunoglobulins", J. Mol. Biol. 196, 901-917, (1987).
Chothia, et al., "Conformations of immunoglobulin hypervariable regions", Nature, vol. 342, 877-883, (Dec. 21, 1989).

(56) References Cited

OTHER PUBLICATIONS

De Genst, et al., "Antibody repertoire development in camelids", Developmental and Comparative Immunology, 30, pp. 187-198, (2006).
Dornan, et al., "Therapeutic potential of an anti-CD79b antibody-drug conjugate, anti-CD79b-vc-MMAE, for the treatment of non-Hodgkin lymphoma", Blood, vol. 114, No. 13, pp. 2721-2729, (Sep. 2009).
Drachman, et al., "The next generation of ADCs", Proceedings: AACR 106th Annual Meeting 2015, Cancer Res. 75 (15 Suppl), Abstract SY35-01 (2015).
Ellison, et al., "Nucleotide Sequence of a Human Immunoglobulin Cγ4 Gene", DNA, vol. 1, No. 1, 11-18, (1981).
Ellison, et al., "The nucleotide sequence of a human immunoglobulin $Cy_1$ gene" Nucleic Acids Research, vol. 10, No. 13, 4071-4079, (1982).
EPO Application No. 13790467.8 (Published as EP2850104), European Search Report and European Search Opinion, 7 pages, (dated Jun. 14, 2016).
EPO Application No. 17767412.4, Supplementary Search Report and Search Opinion, 8 pages, (dated Jul. 9, 2019).
EPO Application No. 18171884.2, European Search Report and European Search Opinion, 7 pages, (dated Nov. 23, 2018).
Erba, et al., "A Phase 1b Study of Vadastuximab Talirine in Combination with 7+3 Induction Therapy for Patients with Newly Diagnosed Acute Myeloid Leukemia (AML)", Blood, 128(22), Abstract No. 211, (2016).
Erba, et al., "SGN-CD33A: case reports of anti-leukemic activity and bridge to allogeneic stem cell transplant (SCT) in patients with acute myeloid leukemia (AML)", Biol. Blood Marrow Transplant 21, (suppl 2), S185-186, (2015).
Fathi, et al., "A phase 1 trial of vadastuximab talirine combined with hypomethylating agents in patients with CD33-positive AML", Blood, vol. 132, No. 11, pp. 1125-1133, (Sep. 13, 2018).
Fathi, et al., "SGN-CD33A in Combination With Hypomethylating Agents: A Novel, Well-Tolerated Regimen With High Remission Rate in Older Patients With AML", Haematologica, 101(s1), pp. 186-187, (2016).
Fathi, et al., "SGN-CD33A plus hypomethylating agents: a novel, well-tolerated regimen with high remission rate in frontline unfit AML", Blood, 126(23), Abstract 454, (Dec. 3, 2015).
Fathi, et al., "Vadastuximab Talirine Plus Hypomethylating Agents: A Well-Tolerated Regimen with High Remission Rate in Frontline Older Patients with Acute Myeloid Leukemia (AML)", Blood, 128(22), Abstract No. 591, (2016).
Feldman, et al, Phase III Randomized Multicenter Study of a Humanized Anti-CD33 Monoclonal Antibody, Lintuzumab, in Combination With Chemotherapy, Versus Chemotherapy Alone in Patients With Refractory or First-Relapsed Acute Myeloid Leukemia, Journal of Clinical Oncology, vol. 23, No. 18, pp. 4110-4116, (Jun. 20, 2005).
Feldman, et al., "Novel Therapeutics for Therapy-Related Acute Myeloid Leukemia: 2014", Clinical Lymphoma, Myeloma & Leukemia, vol. 15, No. S1, pp. S91-S93, (2015).
GenBank, *Homo sapiens* immunoglobulin gamma-1 heavy chain constant region (IGHG1) gene, partial cds, Accession No. J00228.1, (2019).
Griffiths, et al., "Human anti-self antibodies with high specificity from phage display libraries", the EMBO Journal, vol. 12, No. 2, pp. 725-734, (1993).
Hu et al., "Minibody: A Novel Engineered Anti-Carcinoembryonic Antigen Antibody Fragment (Single-Chain Fv-$C_H3$) Which Exhibits Rapid, High-Level Targeting of Xenografts", Cancer Research 56, 3055-3061, (Jul. 1996).
Karlin et al., "DNA Sequence Patterns in Human, Mouse, and Rabbit Immunoglobulin Kappa-Genes", J. Mol. Evol. 22, 195-208, (1985).
Kennedy, et al., "SGN-CD33A: Preclinical and phase 1 interim clinical trial results of a CD33-directed PBD dimer antibody-drug conjugate for the treatment of acute myeloid leukemia (AML)", Proceedings: AACR 106th Annual Meeting 2015, AACR; Cancer Res. 75 (15 Suppl), Abstract DDT02-04, (Apr. 2015).
Kenten, et al., "Cloning and sequence determination of the gene for the human immunoglobulin e chain expressed in a myeloma cell line", Proc. Natl. Acad. Sci. USA, vol. 79, 6661-6665, (Nov. 1982).
Kimka, et al., "Human anti-CD30 recombinant antibodies by guided phage antibody selection using cell panning", British Journal of Cancer, 83(2), pp. 252-260, (2000).
Kindsvogel, et al., "A Cloned cDNA Probe for Rat Immunoglobulin Epsilon Heavy Chain: Construction, Identification, and DNA Sequence", DNA, vol. 1, No. 4, 335-343, (1982).
Kondo, et al., "Signal joint of immunoglobulin Vhl-Jh and novel joints of chimeric V pseudogenes on extrachromosomal circular DNA from chicken bursa", Eur. J. Immunol. 23, 245-249, (1993).
Kung Sutherland, et al., "SGN-CD33A: a novel CD33-directed antibody-drug conjugate, utilizing pyrrolobenzodiazepine dimers, demonstrates preclinical antitumor activity against multi-drug resistant human AML", ASH Annual Meeting Abstracts 120: Abstract 3589, (2012).
Kung Sutherland, et al., "SGN-CD33A: a novel CD33-targeting antibody-drug conjugate using a pyrrolobenzodiazepine dimer is active in models of drug-resistant AML", Blood, 122:1455-1463, (2013).
Lamminmaki, et al., "Protein Structure and Folding: Crystal Structure of a Recombinant Anti-estradiol Fab Fragment in Complex with 17β-Estradiol", J. Biol. Chem., 276: 36687-36694, (2001).
Laszlo, et al., "Cellular determinants for preclinical activity of a novel CD33/CD3 bispecific T-cell engager (BiTE) antibody, AMG 330, against human AML", Blood, vol. 23, No. 4, 554-561, (Jan. 23, 2014).
Levy, et al., "A Phase 1b Study of the Combination of Vadastuximab Talirine and 7+3 Induction Therapy for Patients With Newly Diagnosed Acute Myeloid Leukemia (AML)", Proceedings of the 22nd Congress of the European Hematology Association Madrid Spain, Abstract No. S793, (Jun. 25, 2017).
Lewis, et al., "Abstract 1195: SGN-CD352A: A novel humanized anti-CD352 antibody-drug conjugate for the treatment of multiple myeloma", Cancer Research, 76, Suppl 14, Abstract No. 1195, (2016).
Lu et al., "Fab-scFv fusion protein: an efficient approach to production of bispecific antibody fragments", Journal of Immunological Methods 267, 213-226, (2002).
MacCallum, et al., "Antibody-antigen Interactions: Contact Analysis and Binding Site Topography", J. Mol. Biol., 262:732-745, (1996).
Martin, et al., "Sequence-Selective Interaction of the Minor-Groove lnterstrand Cross-Linking Agent SJG-136 with Naked and Cellular DNA: Footprinting and Enzyme Inhibition Studies", vol. 44, No. 11, 4133-4147, (2005).
Muyldermans, et al., "Unique single-domain antigen binding fragments derived from naturally occurring camel heavy-chain antibodies", Journal of Molecular Recognition 12, 131-140, (1999).
Nand, et al., "A phase 2 trial of azacitidine and gemtuzumab ozogamicin therapy in older patients with acute myeloid leukemia", Blood, 122:3432-3439, (2013).
Nguyen, et al., "Camel heavy-chain antibodies: diverse germline $V_HH$ and specific mechanisms enlarge the antigen-binding repertoire", the EMBO Journal, vol. 19, No. 5, 921-930, (2000).
Pack et al., "Miniantibodies: Use of Amphipathic Helices to Produce Functional, Flexibly Linked Dimeric Fv Fragments with High Avidity in *Escherichia coli*", Biochemistry, vol. 31, No. 6, 1579-1584, (1992).
Padlan, et al. "Anatomy of the Antibody Molecule", Molecular Immunology, vol. 31, No. 3, 169-217, (1994).
Padlan, et al., "Structure of an antibody-antigen complex: Crystal structure of the HyHEL-10 Fab-lysozyme complex", Proc. Natl. Acad. Sci. USA, 86:5938-5942, (1989).
Pascalis et al., "Grafting of "Abbreviated" Complementarity-Determining Regions Containing Specificity-Determining Residues Essential for Ligand Contact to Engineer a Less Immunogenic Humanized Monoclonal Antibody", J. Immunol., 169:3076-3084, (2002).

(56) References Cited

OTHER PUBLICATIONS

PCT Application No. PCT/US2013/041209, International Preliminary Report on Patentability, 7 pages, (dated Apr. 30, 2015).
PCT Application No. PCT/US2013/041209, International Search Report and Written Opinion, 10 pages, (dated Oct. 25, 2013).
PCT Application No. PCT/US2017/022472, International Preliminary Report on Patentability, 8 pages, (dated Sep. 27, 2018).
PCT Application No. PCT/US2017/022472, International Search Report and Written Opinion, 16 pages, (dated Jul. 19, 2017).
PCT Application No. PCT/US2017/027246, International Preliminary Report on Patentability, 8 pages, (dated Oct. 25, 2018).
PCT Application No. PCT/US2017/027246, International Search Report and Written Opinion, 14 pages, (dated Jul. 10, 2017).
PCT Application No. PCT/US2017/035793, International Preliminary Report on Patentability, 7 pages, (dated Dec. 13, 2018).
PCT Application No. PCT/US2017/035793, International Search Report and Written Opinion, 9 pages, (dated Sep. 6, 2017).
PCT Application No. PCT/US2017/036605, International Preliminary Report on Patentability, 11 pages, (dated Dec. 20, 2018).
PCT Application No. PCT/US2017/036605, International Search Report and Written Opinion, 20 pages, (dated Oct. 27, 2017).
Pessi, et al., "A designed metal-binding protein with a novel fold", Nature, vol. 362, 367-369, (1993).
Putnam, "The Plasma Proteins", vol. V, Academic Press, Inc., 49-140, (1987).
Qiu, et al., "Small antibody mimetics comprising two complementarity-determining regions and a framework region for tumor targeting", Nature Biotechnology, vol. 25, No. 8, 921-929, (2007).
Ravandi, et al., "Vadastuximab Talirine Plus Hypomethylating Agents: A Well-Tolerated Regimen With High Remission Rate in Frontline Older Patients With Acute Myeloid Leukemia", Haematologica, 102(s2), (2017).
Reichmann et al., "Reshaping human antibodies for therapy", Nature, vol. 332,323-327, (1988).
Renault, et al., "BAK/BAX activation and cytochrome c release assays using isolated mitochondria", Methods 61, 146-155, (2013).
Rudikoff, et al., "Single amino acid substitution altering antigen-binding specificity", Proc. Natl. Acad. Sci. USA, 79:1979, (1982).
Rusconi, et al., "Transmission and expression of a specific pair of rearranged immunoglobulin μ and k genes in a transgenic mouse line", Nature, vol. 314, 330-334, (1985).
Ryan, et al., "SGN-CD19B, a Pyrrolobenzodiazepine (PBD)-Based Anti-CDI 9 Drug Conjugate, Demonstrates Potent Preclinical Activity Against B-Cell Malignancies", Blood, 126, No. 23. p. 594, (2015).
Seattle Genetics, Inc., Press Release, "Seattle Genetics Presents Phase 1b Data from Vadastuximab Talirine (SGN-CD33A; 33A) in Combination with Standard of Care in Frontline Acute Myeloid Leukemia at ASH Annual Meeting", Available at: https://investor.seattlegenetics.com/press-releases/news-details/2016/Seattle-Genetics-Presents-Phase-1b-Data-from-Vadastuximab-Talirine-SGN-CD33A-33A-in-Combination-with-Standard-of-Care-in-Frontline-Acute-Myeloid-Leukemia-at-ASH-Annual-Meeting/default.aspx, 4 pages, (Dec. 3, 2016).
Seattle Genetics, Inc., Press Release, "Seattle Genetics Discontinues Phase 3 CASCADE Trial of Vadastuximab Talirine (SGN-CD33A) in Frontline Acute Myeloid Leukemia", Available at: https://investor.seattlegenetics.com/press-releases/news-details/2017/Seattle-Genetics-Discontinues-Phase-3-CASCADE-Trial-of-Vadastuximab-Talirine-SGN-CD33A-in-Frontline-Acute-Myeloid-Leukemia/default.aspx, 3 pages, (Jun. 19, 2017).
Seno et al., "Molecular cloning and nudeoddc sequencing of human immunoglobulin e chain cDNA", Nucleic Acids Research, vol. 11, No. 3, 719-726, (1983).
Smellie, et al., "Sequence-Selective Recognition of Duplex DNA through Covalent Interstrand Cross-Linking: Kinetic and Molecular Modeling Studies with Pyrrolobenzodiazepine Dimers", Biochemistry 42, 8232-8239, (2003).

Stein, et al., "A phase 1 trial of SGN-CD33A as monotherapy in patients with CD33-positive acute myeloid leukemia (AML)", Blood, 126(23), Abstract 324, (Dec. 3, 2015).
Stein, et al., "A phase 1 trial of vadastuximab talirine as monotherapy in patients with CD33-positive acute myeloid leukemia", Blood, vol. 131, No. 4, pp. 387-396, (Jan. 25, 2018).
Stein, et al., "Interim analysis of a phase 1 trial of SGN-CD33A in patients with CD33-positive acute myeloid leukemia (AML)", Blood 124(21), Abstract 623, (2014).
Stein, et al., "SGN-CD33A (Vadastuximab Talirine) followed by Allogeneic Hematopoietic Stem Cell Transplant (AlloHSCT) Results in Durable Complete Remissions (CRs) in Patients with Acute Myeloid Leukemia (AML)", Abstracts—Biol Blood Marrow Transplant 22 (suppl 3), pp. 211-212, (2016).
Sutherland, et al., "5-azacytidine enhances the anti-leukemic activity of lintuzumab (SGN-33) in preclinical models of acute myeloid leukemia", mAbs, 2:4 440-448, (2010).
Sutherland, et al., "SGN-CD123A, a Pyrrolobenzodiazepine Dimer Linked Anti-CDI 23 Antibody Drug Conjugate, Demonstrates Effective Anti-Leukemic Activity in Multiple Preclinical Models of AML", Blood, 126:330, (2015).
Sutherland, et al., "Anti-leukemic activity of lintuzumab (SGN-33) in preclinical models of acute myeloid leukemia", mAbs, 1:5, 481-490, (2009).
Sutherland, et al., "SGN-CD33A in Combination with CD33A Hypomethylating Agents is Highly Efficacious in Preclinical Models of AML", Blood, 126(23), Abstract 3785, (2015).
Sutherland, et al., "SGN-CD33A in combination with cytarabine or hypomethylating agents demonstrates enhanced anti-leukemic activity in preclinical models of AML", Blood, 124(21), Abstract No. 3739, (2014).
Sutherland, et al., "SGN-CD33A: a novel CD33-targeting antibody-drug conjugate using a pyrrolobenzodiazepine dimer is active in models of drug-resistant AML", Blood, vol. 122, No. 8, pp. 1455-1463 (Aug. 22, 2013).
Tarlock, et al., "2723 Synergistic Effect of SGN-CD33A and FLT3 Inhibitors in FLT3 /ITD Acute Myeloid Leukemia", Oral and Poster Abstracts No. 2723, ASH Annual Meeting, 2 pgs., (Dec. 2, 2018).
Tarlock, et al., "3942 CD33 SNP Genotype and Splice Variation are Associated with CD33 Cell Surface Expression and SGN-CD33A Pharmacokinetics", Oral and Poster Abstracts No. 3942, ASH Annual Meeting, 2 pgs., (Dec. 3, 2018).
Thurston et al., "Synthesis of Sequence-Selective C8-Linked Pyrrolo[2,1-c][1,4]benzodiazepine DNA Interstrand Cross-Linking Agents", J. Org. Chem. 61, 8141-8147, (1996).
U.S. Appl. No. 13/804,227, Advisory Action dated Nov. 18, 2015.
U.S. Appl. No. 13/804,227, Final Office Action dated Aug. 10, 2015.
U.S. Appl. No. 13/804,227, Non-Final Office Action dated Feb. 18, 2016.
U.S. Appl. No. 13/804,227, Non-Final Office Action dated Feb. 27, 2015.
U.S. Appl. No. 13/804,227, Non-Final Office Action dated Mar. 14, 2016.
U.S. Appl. No. 13/804,227, Restriction Requirement dated Sep. 18, 2014.
U.S. Appl. No. 13/826,007, Non-Final Office Action dated Sep. 11, 2015.
U.S. Appl. No. 14/401,837, Non-Final Office Action dated May 27, 2016.
U.S. Appl. No. 14/401,837, Notice of Allowance dated Oct. 14, 2016.
Vajdos, et al., "Comprehensive Functional Maps of the Antigen-binding Site of an Anti-ErbB2 Antibody Obtained with Shotgun Scanning Mutagenesis", J. Mol. Biol., 320:415-428, (2002).
Van Der Loo, et al., "Characterization and DNA sequence of the b6w2 allotype of the rabbit immunoglobulin kappa 1 light chain (b locus)", Immunogenetics 42, 333-341, (1995).
Walter, et al., "A Phase 1b Study of Vadastuximab Talirine (33A) in Combination with 7+3 Induction Therapy for Patients with Newly Diagnosed Acute Myeloid Leukemia (AML)", Ann. Hematol. 96, Suppl 1, p. 69, (2017).
Wang, et al., "CASCADE: A phase 3, randomized, double-blind study of vadastuximab talirine (33A) versus placebo in combination

(56) References Cited

OTHER PUBLICATIONS with azacitidine or decitabine in the treatment of older patients with newly diagnosed acute myeloid leukemia (AML)", Journal of Clinical Oncology 35, No. 15 suppl, Abstract TPS7066, 1 pg. (2017).

Ward, et al., "Binding activities of a repertoire of single immunoglobulin variable domains secreted from *Escherichia coli*", Nature, vol. 341, pp. 544-546, (Oct. 12, 1989).

Wu, et al., "Humanization of a Murine Monoclonal Antibody by Simultaneous Optimization of Framework and CDR Residues", J. Mol. Biol., 294:151-162, (1999).

Yang, et al., "A Phase 1b Study of Vadastuximab Talirine as Maintenance and in Combination with Standard Consolidation for Patients with Acute Myeloid Leukemia (AML)", Blood, 128(22), Abstract No. 340, (2016).

Yang et al., "Abstract 4589: Preclinical investigation of SGN-CD70A antibody-drug conjugate in T cell lymphomas", Cancer Research, 77, Suppl 13, Abstract No. 4589, (2017).

Zuo, et al., "An efficient route to the production of an IgG-like bispecific antibody", Protein Engineering, vol. 13, No. 5, 361-367, (2000).

EPO Application No. 17783071.8 (Published as EP3442591), European Search Report and European Search Opinion, 9 pages, (dated Oct. 17, 2019).

Jeffrey, et al., "Development of Pyrrolobenzodiazepine-Based Antibody-Drug Conjugates for Cancer", AACR Annual Meeting, Abstract No. 4321, 1 pages, (2013).

\* cited by examiner

FIGURE 2

| ADC | Compound | Test 1: Count of synergistic 3x3 dose blocks (p<0.01, HSA) | | | | | | | | | | | Test 2: Activity Improvement (decrease in percent viability at best dose, EOHSA) | | | | | | | | | | | Test 3: PTCDS (percent of total cytotoxicity due to synergy, all doses tested, HSA) | | | | | | | | | | | Count of models passing tests (cutoff) | | | | | Overall Classification (passed all 3 tests/cutoffs in multiple models) |
|---|---|---|---|---|---|---|---|---|---|---|---|---|---|---|---|---|---|---|---|---|---|---|---|---|---|---|---|---|---|---|---|---|---|---|---|---|---|---|---|
| | | HL60 | HNT-34 | Kasumi1 | KG-1_8031 | KG-1_cb | ME-1 | MOLM13 | MV411 | SKM1 | TF1a | THP-1 | HL60 | HNT-34 | Kasumi1 | KG-1_8031 | KG-1_cb | ME-1 | MOLM13 | MV411 | SKM1 | TF1a | THP-1 | HL60 | HNT-34 | Kasumi1 | KG-1_8031 | KG-1_cb | ME-1 | MOLM13 | MV411 | SKM1 | TF1a | THP-1 | Test 1 (>15) | Test 2 (>20%) | Test 3 (>2%) | All 3 tests | Total tested | |
| SGN-CD33A | ABT-199 | 100 | 50 | 45 | 99 | 76 | 43 | 65 | 96 | 13 | 0 | 87 | 34.3 | 40.6 | 31.0 | 33.2 | 44.0 | 33.0 | 18.6 | 14.4 | 13.7 | 0.0 | 46.4 | 6.7 | 13.2 | 6.7 | 9.3 | 28.7 | 0.6 | 3.6 | 2.2 | 2.8 | -0.9 | 6.1 | 9 | 7 | 9 | 6 | 11 | Synergistic |
| SGN-CD33A | ABT-263 | 116 | 29 | 45 | 132 | 42 | 41 | 43 | 159 | 98 | 49 | 108 | 47.0 | 33.8 | 43.0 | 43.0 | 90.6 | 32.9 | 22.7 | 14.9 | 26.6 | 50.6 | 63.7 | 6.9 | 4.7 | 5.7 | 6.7 | 22.7 | -9.5 | 3.8 | 2.3 | 4.3 | 5.2 | 8.8 | 11 | 10 | 10 | 9 | 11 | Synergistic |
| SGN-CD123A | ABT-199 | 46 | 71 | 50 | 122 | 88 | 72 | 158 | 153 | 77 | 7 | 90 | 33.5 | 27.2 | 44.0 | 42.7 | 56.8 | 34.7 | 17.7 | 13.3 | 27.4 | 19.4 | 49.4 | 7.8 | 5.3 | 10.1 | 11.4 | 19.9 | 4.5 | 3.5 | 2.5 | 6.4 | 0.8 | 21.3 | 10 | 8 | 10 | 8 | 11 | Synergistic |
| SGN-CD123A | ABT-263 | 17 | 72 | 76 | 138 | 101 | 61 | 156 | 145 | 75 | 45 | 90 | 35.8 | 36.5 | 36.5 | 38.4 | 46.7 | 37.9 | 17.1 | 11.3 | 32.2 | 35.4 | 54.2 | 3.2 | 6.1 | 7.1 | 6.8 | 22.4 | 0.7 | 3.1 | 2.3 | 7.6 | 3.2 | 15.1 | 11 | 9 | 10 | 8 | 11 | Synergistic |

FIGURE 3

FIGURE 8
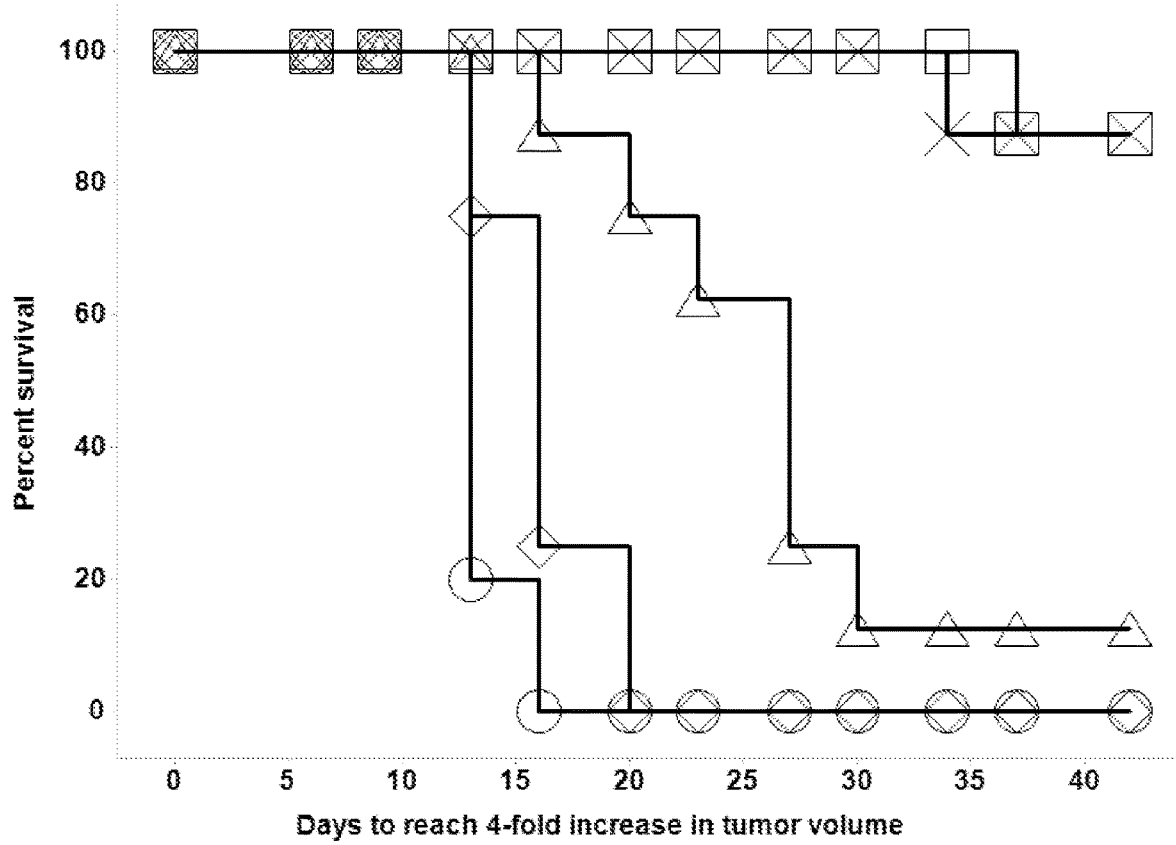
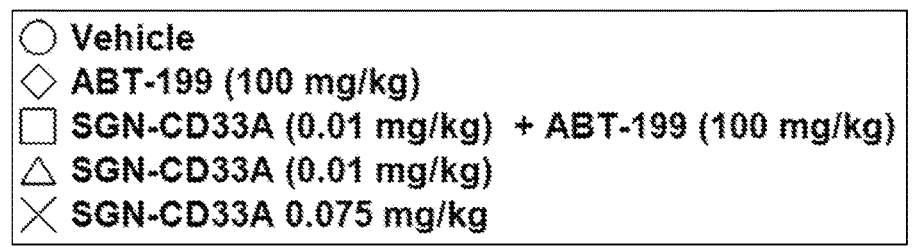

SEQUENCE LISTING

```
<160> NUMBER OF SEQ ID NOS: 15

<210> SEQ ID NO 1
<211> LENGTH: 107
<212> TYPE: PRT
<213> ORGANISM: Artificial Sequence
<220> FEATURE:
<223> OTHER INFORMATION: h2H12 Light chain variable region

<400> SEQUENCE: 1

Asp Ile Gln Met Thr Gln Ser Pro Ser Ser Leu Ser Ala Ser Val Gly
1               5                   10                  15

Asp Arg Val Thr Ile Asn Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                85                  90                  95

Thr Phe Gly Gly Gly Thr Lys Val Glu Ile Lys
            100                 105

<210> SEQ ID NO 2
<211> LENGTH: 117
<212> TYPE: PRT
<213> ORGANISM: Artificial Sequence
<220> FEATURE:
<223> OTHER INFORMATION: 2H12 Heavy chain variable region

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Pro Gly Gln Gly Leu Glu Trp Ile
```

```
                   35                  40                  45

Gly Trp Ile Tyr Pro Gly Asp Gly Ser Thr Lys Tyr Asn Glu Lys Phe
 50                  55                  60

Lys Ala Lys Ala Thr Leu Thr Ala Asp Thr Ser Ser Thr Ala Tyr
 65                  70                  75                  80

Met Glu Leu Arg Ser Leu Arg Ser Asp Asp Thr Ala Val Tyr Tyr Cys
                 85                  90                  95

Ala Ser Gly Tyr Glu Asp Ala Met Asp Tyr Trp Gly Gln Gly Thr Thr
                100                 105                 110

Val Thr Val Ser Ser
            115

<210> SEQ ID NO 3
<211> LENGTH: 106
<212> TYPE: PRT
<213> ORGANISM: Homo sapiens

<400> SEQUENCE: 3

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
             20                  25                  30

Pro Arg Glu Ala Lys Val Gln Trp Lys Val Asp Asn Ala Leu Gln Ser
         35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105

<210> SEQ ID NO 4
<211> LENGTH: 330
<212> TYPE: PRT
<213> ORGANISM: Homo sapiens

<400> SEQUENCE: 4

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
```

```
                    130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 5
<211> LENGTH: 329
<212> TYPE: PRT
<213> ORGANISM: Homo sapiens

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

-continued

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 6
<211> LENGTH: 330
<212> TYPE: PRT
<213> ORGANISM: Homo sapiens

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 7
<211> LENGTH: 329
<212> TYPE: PRT
<213> ORGANISM: Homo sapiens

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

```
                260                 265                 270
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 8
<211> LENGTH: 120
<212> TYPE: PRT
<213> ORGANISM: Artificial Sequence
<220> FEATURE:
<223> OTHER INFORMATION: h7G3 Heavy chain variable region

<400> SEQUENCE: 8

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120

<210> SEQ ID NO 9
<211> LENGTH: 114
<212> TYPE: PRT
<213> ORGANISM: Artificial Sequence
<220> FEATURE:
<223> OTHER INFORMATION: h7G3 Light chain variable region

<400> SEQUENCE: 9

Asp Phe Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Leu Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110
```

Lys Arg

<210> SEQ ID NO 10
<211> LENGTH: 107
<212> TYPE: PRT
<213> ORGANISM: Artificial Sequence
<220> FEATURE:
<223> OTHER INFORMATION: hBU12 Light chain variable region

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Val Ala Val Tyr Tyr Cys Phe Gln Gly Ser Val Tyr Pro Phe Thr
                85                  90                  95

Phe Gly Gln Gly Thr Lys Leu Glu Ile Lys Arg
            100                 105

<210> SEQ ID NO 11
<211> LENGTH: 120
<212> TYPE: PRT
<213> ORGANISM: Artificial Sequence
<220> FEATURE:
<223> OTHER INFORMATION: hBU12 Heavy chain variable region

<400> SEQUENCE: 11

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Ser Thr Ser
            20                  25                  30

Gly Met Gly Val Gly Trp Ile Arg Gln His Pro Gly Lys Gly Leu Glu
        35                  40                  45

Trp Ile Gly His Ile Trp Trp Asp Asp Lys Arg Tyr Asn Pro Ala
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser
        115                 120

<210> SEQ ID NO 12
<211> LENGTH: 298
<212> TYPE: PRT
<213> ORGANISM: Artificial Sequence
<220> FEATURE:
<223> OTHER INFORMATION: h1F6 Light chain variable region

<400> SEQUENCE: 12

Ala Ser Pro Ile Leu Glu Val Ala Leu Met Glu Thr Thr His Arg Gly
1               5                   10                  15

Leu Asn Ser Glu Arg Pro Ala Ser Pro Ser Glu Arg Leu Ala Leu Ala
            20                  25                  30

Val Ala Leu Ser Glu Arg Leu Gly Leu Tyr Glu Ala Arg Gly Ala Leu
        35                  40                  45

Ala Thr His Arg Ile Leu Glu Ala Ser Asn Cys Tyr Ser Ala Arg Gly
    50                  55                  60

Ala Leu Ala Ser Glu Arg Leu Tyr Ser Ser Glu Arg Val Ala Leu Ser
65                  70                  75                  80

Glu Arg Thr His Arg Ser Glu Arg Gly Leu Tyr Thr Tyr Arg Ser Glu
                85                  90                  95

Arg Pro His Glu Met Glu Thr His Ile Ser Thr Arg Pro Thr Tyr Arg
            100                 105                 110

Gly Leu Asn Gly Leu Asn Leu Tyr Ser Pro Gly Leu Tyr Gly Leu Asn
        115                 120                 125

Pro Pro Leu Tyr Ser Leu Leu Ile Leu Glu Thr Tyr Arg Leu Ala Leu
    130                 135                 140

Ala Ser Glu Arg Ala Ser Asn Leu Glu Ser Glu Arg Gly Leu Tyr Val
145                 150                 155                 160

Ala Leu Pro Ala Ser Pro Ala Arg Gly Pro His Glu Ser Glu Arg Gly
                165                 170                 175

Leu Tyr Ser Glu Arg Gly Leu Tyr Ser Glu Arg Gly Leu Tyr Thr His
            180                 185                 190

Arg Ala Ser Pro Pro His Glu Thr His Arg Leu Thr His Arg Ile Leu
        195                 200                 205

Glu Ser Glu Arg Ser Glu Arg Leu Gly Leu Asn Ala Leu Ala Glu Ala
    210                 215                 220

Ser Pro Val Ala Leu Ala Leu Ala Val Ala Leu Thr Tyr Arg Thr Tyr
225                 230                 235                 240

Arg Cys Tyr Ser Gly Leu Asn His Ile Ser Ser Glu Arg Ala Arg Gly
                245                 250                 255

Glu Val Ala Leu Pro Thr Arg Pro Thr His Arg Pro His Glu Gly Leu
            260                 265                 270

Tyr Gly Leu Asn Gly Leu Tyr Thr His Arg Leu Tyr Ser Val Ala Leu
        275                 280                 285

Glu Ile Leu Glu Leu Tyr Ser Ala Arg Gly
    290                 295

<210> SEQ ID NO 13
<211> LENGTH: 334
<212> TYPE: PRT
<213> ORGANISM: Artificial Sequence
<220> FEATURE:
<223> OTHER INFORMATION: h1F6 Heavy chain variable region

<400> SEQUENCE: 13

Gly Leu Asn Val Ala Leu Gly Leu Asn Leu Val Ala Leu Gly Leu Asn
1               5                   10                  15

Ser Glu Arg Gly Leu Tyr Ala Leu Ala Glu Val Ala Leu Leu Tyr Ser
            20                  25                  30

Leu Tyr Ser Pro Gly Leu Tyr Ala Leu Ala Ser Glu Arg Val Ala Leu
        35                  40                  45

Leu Tyr Ser Val Ala Leu Ser Glu Arg Cys Tyr Ser Leu Tyr Ser Ala
    50                  55                  60

Leu Ala Ser Glu Arg Gly Leu Tyr Thr Tyr Arg Thr His Arg Pro His
65                  70                  75                  80

Glu Thr His Arg Ala Ser Asn Thr Tyr Arg Gly Leu Tyr Met Glu Thr
            85                  90                  95

Ala Ser Asn Thr Arg Pro Val Ala Leu Ala Arg Gly Gly Leu Asn Ala
            100                 105                 110

Leu Ala Pro Gly Leu Tyr Gly Leu Asn Gly Leu Tyr Leu Leu Tyr Ser
            115                 120                 125

Thr Arg Pro Met Glu Thr Gly Leu Tyr Thr Arg Pro Ile Leu Glu Ala
            130                 135                 140

Ser Asn Thr His Arg Thr Tyr Arg Thr His Arg Gly Leu Tyr Glu Pro
145                 150                 155                 160

Thr His Arg Thr Tyr Arg Ala Leu Ala Ala Ser Pro Ala Leu Ala Pro
            165                 170                 175

His Glu Leu Tyr Ser Gly Leu Tyr Ala Arg Gly Val Ala Leu Thr His
            180                 185                 190

Arg Met Glu Thr Thr His Arg Ala Arg Gly Ala Ser Pro Thr His Arg
            195                 200                 205

Ser Glu Arg Ile Leu Glu Ser Glu Arg Thr His Arg Ala Leu Ala Thr
            210                 215                 220

Tyr Arg Met Glu Thr Glu Leu Ser Glu Arg Ala Arg Gly Leu Ala Arg
225                 230                 235                 240

Gly Ser Glu Arg Ala Ser Pro Ala Ser Pro Thr His Arg Ala Leu Ala
            245                 250                 255

Val Ala Leu Thr Tyr Arg Thr Tyr Arg Cys Tyr Ser Ala Leu Ala Ala
            260                 265                 270

Arg Gly Ala Ser Pro Thr Tyr Arg Gly Leu Tyr Ala Ser Pro Thr Tyr
            275                 280                 285

Arg Gly Leu Tyr Met Glu Thr Ala Ser Pro Thr Tyr Arg Thr Arg Pro
            290                 295                 300

Gly Leu Tyr Gly Leu Asn Gly Leu Tyr Thr His Arg Thr His Arg Val
305                 310                 315                 320

Ala Leu Thr His Arg Val Ala Leu Ser Glu Arg Ser Glu Arg
            325                 330

<210> SEQ ID NO 14
<211> LENGTH: 107
<212> TYPE: PRT
<213> ORGANISM: Artificial Sequence
<220> FEATURE:
<223> OTHER INFORMATION: h20F3 Light chain variable region

<400> SEQUENCE: 14

Gln Ile Val Leu Ser Gln Ser Pro Ala Thr Leu Ser Leu Ser Pro Gly
1               5                   10                  15

Glu Arg Ala Thr Met Ser Cys Arg Ala Ser Ser Val Ser His Met
            20                  25                  30

His Trp Tyr Gln Gln Lys Pro Gly Gln Ala Pro Arg Pro Trp Ile Tyr
            35                  40                  45

Ala Thr Ser Asn Leu Ala Ser Gly Val Pro Ala Arg Phe Ser Gly Ser
            50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Thr Pro Arg Thr
            85                  90                  95

Phe Gly Gly Gly Thr Lys Val Glu Ile Lys Arg
            100                 105

```
<210> SEQ ID NO 15
<211> LENGTH: 118
<212> TYPE: PRT
<213> ORGANISM: Artificial Sequence
<220> FEATURE:
<223> OTHER INFORMATION: h20F3 Heavy chain variable region

<400> SEQUENCE: 15

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Asp Leu Lys Trp Met
            35                  40                  45

Gly Trp Ile Asn Thr Tyr Ser Gly Glu Pro Arg Tyr Ala Asp Asp Phe
        50                  55                  60

Lys Gly Arg Phe Val Phe Ser Leu Asp Lys Ser Val Asn Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Gly Arg Trp Tyr Phe Asp Val Trp Gly Gln Gly Thr
                100                 105                 110

Thr Val Thr Val Ser Ser
            115
```

COMBINATIONS OF PBD-BASED ANTIBODY DRUG CONJUGATES WITH BCL-2 INHIBITORS

CROSS-REFERENCES TO RELATED APPLICATIONS

This application is a U.S. national stage filing under 35 U.S.C. § 371 of International Application No. PCT/US2017/022472, filed Mar. 15, 2017, which claims the benefit of U.S. Provisional Application No. 62/308,778 filed Mar. 15, 2016, U.S. Provisional Application No. 62/356,814 filed Jun. 30, 2016, and U.S. Provisional Application No. 62/428,770 filed Dec. 1, 2016, all of which are hereby incorporated by reference in their entirety for all purposes.

REFERENCE TO A SEQUENCE LISTING

A sequence listing designated 0033-00413PC Sequence Listing.ST25.txt of 27 KB created Mar. 15, 2017, is incorporated herein by reference.

FIELD OF THE INVENTION

This invention relates to treatment of cancer using an antibody drug conjugate comprising a PBD cytotoxic agent in combination with Bcl-2 inhibitors.

BACKGROUND OF THE INVENTION

Antibody drug conjugates (ADCCs) have been shown to be effective at delivering cytotoxic agents to cells that express an antigen recognized by the antibody component of the ADC, e.g., cancer cells. While ADCs have demonstrated activity in the clinic, not all patients respond to single agent ADCs. This application solves these and other problems.

BRIEF SUMMARY OF THE INVENTION

This disclosure provides a method of treating cancer by administering an antibody drug conjugate (ADC) and a Bcl-2 inhibitor. The ADC comprises an antibody that binds to an antigen on a cancer cell and a PBD cytotoxic agent. Antibodies are antibodies that specifically bind to proteins expressed on cancer cells, e.g., CD33, CD123, CD19, CD70 and CD352. Exemplary Bcl-2 inhibitors are ABT-199 and ABT-263.

The PBD cytotoxic agent has the formula

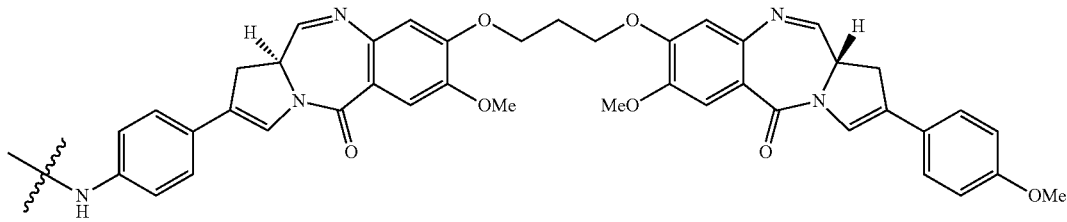 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

A formula of the an antibody (Ab) conjugated to the PBD molecule, including a linker has the formula

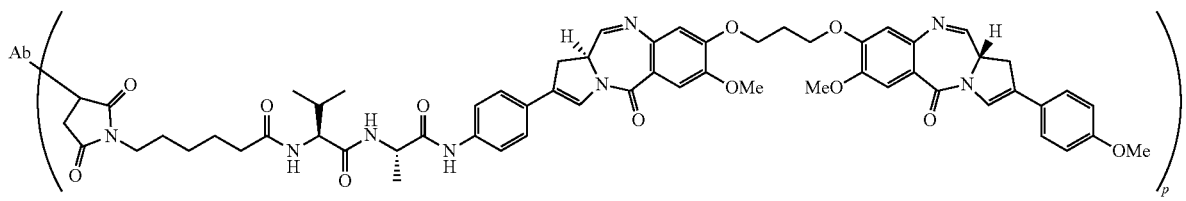

In one embodiment the ADC that includes a PBD cytotoxic agent is administered with the Bcl-2 inhibitor ABT-199, also known as venetoclax. In another embodiment, the ADC that includes a PBD cytotoxic agent is administered with the Bcl-2 inhibitor ABT-263, also known as navetoclax.

In one embodiment, the ADC includes a PBD agent and an antibody that specifically binds to the human CD33 protein. This ADC is administered in combination with a Bcl-2 inhibitor to treat cancer in a subject that has a CD33 positive cancer. In a further embodiment, the antibody is a h2H12 antibody. In another embodiment, the antibody is a h2H12EC antibody. In another embodiment, the Bcl-2 inhibitor is ABT-199 also known as venetoclax. In a further embodiment, the CD33 positive cancer is acute myeloid leukemia or myelodysplastic syndrome.

In one embodiment, the ADC includes a PBD agent and an antibody that specifically binds to the human CD123 protein. This ADC is administered in combination with a Bcl-2 inhibitor to treat cancer in a subject that has a CD123 positive cancer. In a further embodiment, the antibody is the h7G3 antibody. In another embodiment, the antibody is a h7G3EC antibody. In another embodiment, the Bcl-2 inhibitor is ABT-199 also known as venetoclax. In a further embodiment, the CD123 positive cancer is acute myeloid leukemia or myelodysplastic syndrome.

In one embodiment, the ADC includes a PBD agent and an antibody that specifically binds to the human CD19 protein. This ADC is administered in combination with a Bcl-2 inhibitor to treat cancer in a subject that has a CD19 positive cancer. In a further embodiment, the antibody is the hBU12 antibody. In another embodiment, the antibody is an hBU12EC antibody. In another embodiment, the Bcl-2 inhibitor is ABT-199 also known as venetoclax. In a further embodiment, the CD19 positive cancer is non-Hodgkin's lymphoma (NHL), e.g., diffuse large B-cell lymphoma (DLBCL), acute lymphocytic leukemia (ALL), or chronic lymphocytic lymphoma (CLL).

Definitions

A "polypeptide" or "polypeptide chain" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "antibody" is used herein to denote an immunoglobulin protein produced by the body in response to the presence of an antigen and that bind to the antigen. The term also includes antigen-binding fragments and engineered variants thereof. Hence, the term "antibody" includes, for example, intact monoclonal antibodies comprising full-length immunoglobulin heavy and light chains (e.g., antibodies produced using hybridoma technology) and antigen-binding antibody fragments, such as F(ab')2 and Fab fragments. Genetically engineered intact antibodies and fragments, such as chimeric antibodies, humanized antibodies, single-chain Fv fragments, single-chain antibodies, diabodies, minibodies, linear antibodies, multivalent and multispecific (e.g., bispecific) hybrid antibodies, and the like, are also included. Thus, the term "antibody" is used expansively to include any protein that comprises an antigen-binding site of an antibody and is capable of specifically binding to its antigen.

The term "genetically engineered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics such as, e.g., complement fixation, interaction with cells, and other effector functions. Typically, changes in the variable region will be made in order to improve the antigen-binding characteristics, improve variable region stability, or reduce the risk of immunogenicity.

An "antigen-binding site of an antibody" is that portion of an antibody that is sufficient to bind to its antigen. The minimum size of such a region is typically a variable domain or a genetically engineered variant thereof. Single-domain binding sites can be generated from camelid antibodies (see Muyldermans and Lauwereys, *J. Mol. Recog.* 12:131-140, 1999; Nguyen et al., *EMBO J.* 19:921-930, 2000) or from VH domains of other species to produce single-domain antibodies ("dAbs"; see Ward et al., *Nature* 341:544-546, 1989; U.S. Pat. No. 6,248,516 to Winter et al.). In certain variations, an antigen-binding site is a polypeptide region having only 2 complementarity determining regions (CDRs) of a naturally or non-naturally (e.g., mutagenized) occurring heavy chain variable domain or light chain variable domain, or combination thereof (see, e.g., Pessi et al., *Nature* 362: 367-369, 1993; Qiu et al., *Nature Biotechnol.* 25:921-929, 2007). More commonly, an antigen-binding site of an antibody comprises both a heavy chain variable (VH) domain and a light chain variable (VL) domain that bind to a common epitope. Within the context of the present invention, an antibody may include one or more components in addition to an antigen-binding site, such as, for example, a second antigen-binding site of an antibody (which may bind to the same or a different epitope or to the same or a different antigen), a peptide linker, an immunoglobulin constant region, an immunoglobulin hinge, an amphipathic helix (see Pack and Pluckthun, *Biochem.* 31:1579-1584, 1992), a non-peptide linker, an oligonucleotide (see Chaudri et al., *FEBS Letters* 450:23-26, 1999), a cytostatic or cytotoxic drug, and the like, and may be a monomeric or multimeric protein. Examples of molecules comprising an antigen-binding site of an antibody are known in the art and include, for example, Fv, single-chain Fv (scFv), Fab, Fab', F(ab')2, F(ab)c, diabodies, dAbs, minibodies, nanobodies, Fab-scFv fusions, bispecific (scFv)4-IgG, and bispecific (scFv)2-Fab. (See, e.g., Hu et al., *Cancer Res.* 56:3055-3061, 1996; Atwell et al., *Molecular Immunology* 33:1301-1312, 1996; Carter and Merchant, *Curr. Opin. Biotechnol.* 8:449-454, 1997; Zuo et al., *Protein Engineering* 13:361-367, 2000; and Lu et al., *J. Immunol. Methods* 267:213-226, 2002.)

As used herein, the term "immunoglobulin" refers to a protein consisting of one or more polypeptides substantially encoded by immunoglobulin gene(s). One form of immunoglobulin constitutes the basic structural unit of native (i.e., natural) antibodies in vertebrates. This form is a tetramer and consists of two identical pairs of immunoglobulin chains, each pair having one light chain and one heavy chain. In each pair, the light and heavy chain variable regions (VL and VH) are together primarily responsible for binding to an antigen, and the constant regions are primarily responsible for the antibody effector functions. Five classes of immunoglobulin protein (IgG, IgA, IgM, IgD, and IgE) have been identified in higher vertebrates. IgG comprises the major class; it normally exists as the second most abundant protein found in plasma. In humans, IgG consists of four subclasses, designated IgG1, IgG2, IgG3, and IgG4. The heavy chain constant regions of the IgG class are identified with the Greek symbol γ. For example, immunoglobulins of the IgG1 subclass contain a γ1 heavy chain constant region. Each immunoglobulin heavy chain possesses a constant region that consists of constant region protein domains (CH1, hinge, CH2, and CH3; IgG3 also contains a CH4 domain) that are essentially invariant for a given subclass in a species. DNA sequences encoding human and non-human immunoglobulin chains are known in the art. (See, e.g., Ellison et al., *DNA* 1:11-18, 1981; Ellison et al., *Nucleic Acids Res.* 10:4071-4079, 1982; Kenten et al., *Proc. Natl. Acad. Sci. USA* 79:6661-6665, 1982; Seno et al., *Nuc. Acids Res.* 11:719-726, 1983; Riechmann et al., *Nature* 332:323-327, 1988; Amster et al., *Nuc. Acids Res.* 8:2055-2065, 1980; Rusconi and Kohler, *Nature* 314:330-334, 1985; Boss et al., *Nuc. Acids Res.* 12:3791-3806, 1984; Bothwell et al., *Nature* 298:380-382, 1982; van der Loo et al., *Immunogenetics* 42:333-341, 1995; Karlin et al., *J. Mol. Evol.* 22:195-208, 1985; Kindsvogel et al., *DNA* 1:335-343, 1982; Breiner et al., *Gene* 18:165-174, 1982; Kondo et al., *Eur. J. Immunol.* 23:245-249, 1993; and GenBank Accession No. J00228.) For a review of immunoglobulin structure and function, see Putnam, *The Plasma Proteins*, Vol V, Academic Press, Inc., 49-140, 1987; and Padlan, *Mol. Immunol.* 31:169-217, 1994. The term "immunoglobulin" is used herein for its common meaning, denoting an intact antibody, its component chains, or fragments of chains, depending on the context.

Full-length immunoglobulin "light chains" (about 25 Kd or 214 amino acids) are encoded by a variable region gene at the amino-terminus (encoding about 110 amino acids) and by a kappa or lambda constant region gene at the carboxyl-terminus. Full-length immunoglobulin "heavy chains" (about 50 Kd or 446 amino acids) are encoded by a variable region gene (encoding about 116 amino acids) and a gamma, mu, alpha, delta, or epsilon constant region gene (encoding about 330 amino acids), the latter defining the antibody's isotype as IgG, IgM, IgA, IgD, or IgE, respectively. Within light and heavy chains, the variable and constant regions are joined by a "J" region of about 12 or more amino acids, with the heavy chain also including a "D" region of about 10 more amino acids. (*See generally Fundamental Immunology* (Paul, ed., Raven Press, N.Y., 2nd ed. 1989), Ch. 7).

An immunoglobulin light or heavy chain variable region (also referred to herein as a "light chain variable domain" ("VL domain") or "heavy chain variable domain" ("VH domain"), respectively) consists of a "framework" region interrupted by three hypervariable regions, also called "complementarity determining regions" or "CDRs." The framework regions serve to align the CDRs for specific binding to an epitope of an antigen. Thus, the term "hypervariable region" or "CDR" refers to the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917, 1987; Chothia et al., *Nature* 342:878-883, 1989. Kabat also provides a widely used numbering convention (Kabat numbering) in which corresponding residues between different heavy chains or between different light chains are assigned the same number. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3.

Unless the context dictates otherwise, the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

The term "chimeric antibody" refers to an antibody having variable domains derived from a first species and constant regions derived from a second species. Chimeric immunoglobulins or antibodies can be constructed, for example by genetic engineering, from immunoglobulin gene segments belonging to different species. The term "humanized antibody," as defined infra, is not intended to encompass chimeric antibodies. Although humanized antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

The term "humanized VH domain" or "humanized VL domain" refers to an immunoglobulin VH or VL domain comprising some or all CDRs entirely or substantially from a non-human donor immunoglobulin (e.g., a mouse or rat) and variable region framework sequences entirely or substantially from human immunoglobulin sequences. The non-human immunoglobulin providing the CDRs is called the "donor" and the human immunoglobulin providing the framework is called the "acceptor." In some instances, humanized antibodies may retain non-human residues within the human variable domain framework regions to enhance proper binding characteristics (e.g., mutations in the frameworks may be required to preserve binding affinity when an antibody is humanized).

A "humanized antibody" is an antibody comprising one or both of a humanized VH domain and a humanized VL domain. Immunoglobulin constant region(s) need not be present, but if they are, they are entirely or substantially from human immunoglobulin constant regions.

A CDR in a humanized antibody is "substantially from" a corresponding CDR in a non-human antibody when at least 60%, at least 85%, at least 90%, at least 95% or 100% of corresponding residues (as defined by Kabat) are identical between the respective CDRs. In particular, variations of a humanized VH or VL domain in which CDRs are substantially from a non-human immunoglobulin, the CDRs of the humanized VH or VL domain have no more than six (e.g., no more than five, no more than four, no more than three, no more than two, or nor more than one) amino acid substitutions across all three CDRs relative to the corresponding non-human VH or VL CDRs. The variable region framework sequences of an antibody VH or VL domain or, if present, a sequence of an immunoglobulin constant region, are "substantially from" a human VH or VL framework sequence or human constant region, respectively, when at least 85%, at least 90%, at least 95%, or 100% of corresponding residues defined by Kabat are identical. Hence, all parts of a humanized antibody, except possibly the CDRs, are entirely or substantially from corresponding parts of natural human immunoglobulin sequences.

Specific binding of an antibody to its target antigen means an affinity of at least $10^6$, $10^7$, $10^8$, $10^9$, or $10^{10}$ M$^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not, however, necessarily imply that a monoclonal antibody binds one and only one target.

With regard to proteins as described herein, reference to amino acid residues corresponding to those specified by SEQ ID NO includes post-translational modifications of such residues.

The term "anti-CD33 antibody" refers to an antibody that specifically binds to the human CD33 protein. In a preferred embodiment the anti-CD33 antibody comprises the CDRs of the light chain variable region of SEQ ID NO:1 and the CDRs of the heavy chain variable region of SEQ ID NO:2. In another preferred embodiment, the anti-CD33 antibody comprises the light chain variable region of SEQ ID NO:1 and the heavy chain variable region of SEQ ID NO:2. In other preferred embodiments the anti-CD33 antibody includes a human constant region and is an IgG1 antibody. In another preferred embodiment, the anti-CD33 antibody comprises a heavy chain constant region with an S239C substitution using the EU index according to Kabat for amino acid numbering. Examples of such heavy chain constant regions are shown in, e.g., SEQ ID NOs:6 and 7.

The term "anti-CD123 antibody" refers to an antibody that specifically binds to the human CD123 protein. In a preferred embodiment the anti-CD123 antibody comprises the CDRs of the light chain variable region of SEQ ID NO:9 and the CDRs of the heavy chain variable region of SEQ ID NO:8. In another preferred embodiment, the anti-CD123 antibody comprises the light chain variable region of SEQ ID NO:9 and the heavy chain variable region of SEQ ID NO:8. In other preferred embodiments the anti-CD123 antibody includes a human constant region and is an IgG1 antibody. In another preferred embodiment, the anti-CD123 antibody comprises a heavy chain constant region with an S239C substitution using the EU index according to Kabat for amino acid numbering. Examples of such heavy chain constant regions are shown in, e.g., SEQ ID NOs:6 and 7.

The term "anti-CD19 antibody" refers to an antibody that specifically binds to the human CD19 protein. In a preferred embodiment the anti-CD19 antibody comprises the CDRs of the light chain variable region of SEQ ID NO:10 and the CDRs of the heavy chain variable region of SEQ ID NO:11. In another preferred embodiment, the anti-CD19 antibody comprises the light chain variable region of SEQ ID NO:10 and the heavy chain variable region of SEQ ID NO:11. In other preferred embodiments the anti-CD19 antibody includes a human constant region and is an IgG1 antibody. In another preferred embodiment, the anti-CD19 antibody comprises a heavy chain constant region with an S239C substitution using the EU index according to Kabat for amino acid numbering. Examples of such heavy chain constant regions are shown in, e.g., SEQ ID NOs:6 and 7.

The term "anti-CD70 antibody" refers to an antibody that specifically binds to the human CD70 protein. In a preferred embodiment the anti-CD70 antibody comprises the CDRs of the light chain variable region of SEQ ID NO:12 and the CDRs of the heavy chain variable region of SEQ ID NO:13. In another preferred embodiment, the anti-CD70 antibody comprises the light chain variable region of SEQ ID NO:12 and the heavy chain variable region of SEQ ID NO:13. In other preferred embodiments the anti-CD70 antibody includes a human constant region and is an IgG1 antibody. In another preferred embodiment, the anti-CD70 antibody comprises a heavy chain constant region with an S239C substitution using the EU index according to Kabat for amino acid numbering. Examples of such heavy chain constant regions are shown in, e.g., SEQ ID NOs:6 and 7.

The term "anti-CD352 antibody" refers to an antibody that specifically binds to the human CD352 protein. In a preferred embodiment the anti-CD352 antibody comprises the CDRs of the light chain variable region of SEQ ID NO:14 and the CDRs of the heavy chain variable region of SEQ ID NO:15. In another preferred embodiment, the anti-CD352 antibody comprises the light chain variable region of SEQ ID NO:14 and the heavy chain variable region of SEQ ID NO:15. In other preferred embodiments the anti-CD70 antibody includes a human constant region and is an IgG1 antibody. In another preferred embodiment, the anti-CD352 antibody comprises a heavy chain constant region with an S239C substitution using the EU index according to Kabat for amino acid numbering. Examples of such heavy chain constant regions are shown in, e.g., SEQ ID NOs:6 and 7.

An antibody-drug conjugate (ADC) is an antibody conjugated to a cytotoxic drug typically via a linker. The linker may comprise a cleavable unit or may be non-cleavable. Cleavable units include, for example, disulfide-containing linkers that are cleavable through disulfide exchange, acid-labile linkers that are cleavable at acidic pH, and linkers that are cleavable by hydrolases, esterases, peptidases, and glucoronidases (e.g., peptide linkers and glucoronide linkers). Non-cleavable linkers are believed to release drug via a proteolytic antibody degradation mechanism.

The term "diluent" as used herein refers to a solution suitable for altering or achieving an exemplary or appropriate concentration or concentrations as described herein.

The term "container" refers to something into which an object or liquid can be placed or contained, e.g., for storage (for example, a holder, receptacle, vessel, or the like).

The term "administration route" includes art-recognized administration routes for delivering a therapeutic protein such as, for example, parenterally, intravenously, intramuscularly, or subcutaneously. For administration of an ADC for the treatment of cancer, administration into the systemic circulation by intravenous or subcutaneous administration may be desired. For treatment of a cancer characterized by a solid tumor, administration can also be localized directly into the tumor, if so desired.

The term "treatment" refers to the administration of a therapeutic agent to a patient, who has a disease, with the purpose to cure, heal, alleviate, delay, relieve, alter, remedy, ameliorate, improve or affect the disease.

The term "patient" includes human and other mammalian subjects that receive either prophylactic or therapeutic treatment.

The term "effective amount," "effective dose," or "effective dosage" refers to an amount that is sufficient to achieve or at least partially achieve the desired effect, e.g., sufficient to inhibit the occurrence or ameliorate one or more symptoms of a disease or disorder. An effective amount of a pharmaceutical composition is administered in an "effective regime." The term "effective regime" refers to a combination of amount of the composition being administered and dosage frequency adequate to accomplish prophylactic or therapeutic treatment of the disease or disorder.

The term "dosage unit form" (or "unit dosage form") as used herein refers to a physically discrete unit suitable as unitary dosages for a patient to be treated, each unit containing a predetermined quantity of active compound (an ADC in accordance with the present invention) calculated to produce the desired therapeutic effect in association with the required pharmaceutical carrier, diluent, or excipient. The specification for the dosage unit forms of the invention are dictated by and directly dependent on the unique characteristics of the active compound and the particular therapeutic effect to be achieved, and the limitations inherent in the art of compounding such an active compound for the treatment of patients.

Actual dosage levels of an ADC in a formulation of the present invention may be varied so as to obtain an amount of the ADC that is effective to achieve a desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well-known in the medical arts.

The phrase "pharmaceutically acceptable salt," as used herein, refers to pharmaceutically acceptable organic or inorganic salts of a compound. The compound can contain at least one amino group, and accordingly acid addition salts can be formed with the amino group. Exemplary salts include, but are not limited to, sulfate, trifluoroacetate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

A "cytotoxic effect" refers to the depletion, elimination and/or the killing of a target cell. A "cytotoxic agent" refers to an agent that has a cytotoxic effect on a cell.

A "cytostatic effect" refers to the inhibition of cell proliferation. A "cytostatic agent" refers to an agent that has a cytostatic effect on a cell, thereby inhibiting the growth and/or expansion of a specific subset of cells.

Two amino acid sequences have "100% amino acid sequence identity" if the amino acid residues of the two amino acid sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art. (See, e.g., Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in *Methods in Gene Biotechnology* 123-151 (CRC Press, Inc. 1997); Bishop (ed.), *Guide to Human Genome Computing* (2nd ed., Academic Press, Inc. 1998).) Two amino acid sequences are considered to have "substantial sequence identity" if the two sequences have at least 80%, at least 85%, at least 90%, or at least 95% sequence identity relative to each other.

Percentage sequence identities are determined with antibody sequences maximally aligned by the Kabat numbering convention, i.e., the EU index according to Kabat. After alignment, if a subject antibody region (e.g., the entire variable domain of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

The term "pharmaceutical formulation" refers to a preparation which is in such form as to permit the biological activity of the active ingredient to be effective (when administered to a subject), and which contains no additional components which are unacceptably toxic to a subject to which the formulation would be administered. Such formulations are sterile.

Compositions or methods "comprising" one or more recited elements may include other elements not specifically recited.

Reference to a numerical range herein (e.g., "X to Y" or "from X to Y") includes the endpoints defining the range and all values falling within the range.

As used herein, the term "about" denotes an approximate range of plus or minus 10% from a specified value. For instance, the language "about 20%" encompasses a range of 18-22%. As used herein, about also includes the exact amount. Hence "about 20%" means "about 20%" and also "20%."

BRIEF DESCRIPTION OF THE DRAWINGS

FIG. 2 provides data and analysis used to identify synergistic drug combinations.

FIG. 3 provides a summary of the data and analysis used to identify synergistic drug combinations.

FIGS. 4a-d are the exact same data analyzed according to four different models used to assess drug cooperation: 4a. highest single agent (HSA) no fit; 4b. HSA; 4c. Loewe Additivity; and 4d. Bliss Independence.

FIGS. 5a-d are the exact same data analyzed according to four different models used to assess drug cooperation: 5a. highest single agent (HSA) no fit; 5b. HSA; 5c. Loewe Additivity; and 5d. Bliss Independence.

FIGS. 6a-d are the exact same data analyzed according to four different models used to assess drug cooperation: 6a. highest single agent (HSA) no fit; 6b. HSA; 6c. Loewe Additivity; and 6d. Bliss Independence.

FIG. 8 provides the results of a xenograft experiment using a vehicle control, ABT-199, a CD33-ADC comprising a PBD, or a combination of ABT-199 and a CD33-ADC comprising a PBD.

FIG. 10a shows cytotoxicity improvement of best dose combination. FIG. 10b shows statistically significant synergistic 3×3 dose blocks. FIG. 10c shows percent of cytotoxicity due to synergy. CD-ADCs comprising PBDs were tested with ABT-199 on Burkitt's lymphoma cells, DLBCL cells, or folecular lymphoma cells. Data was assessed using three models: highest single agent (HSA) no fit; HSA; Loewe Additivity; and Bliss Independence.

DETAILED DESCRIPTION

Figure 1:
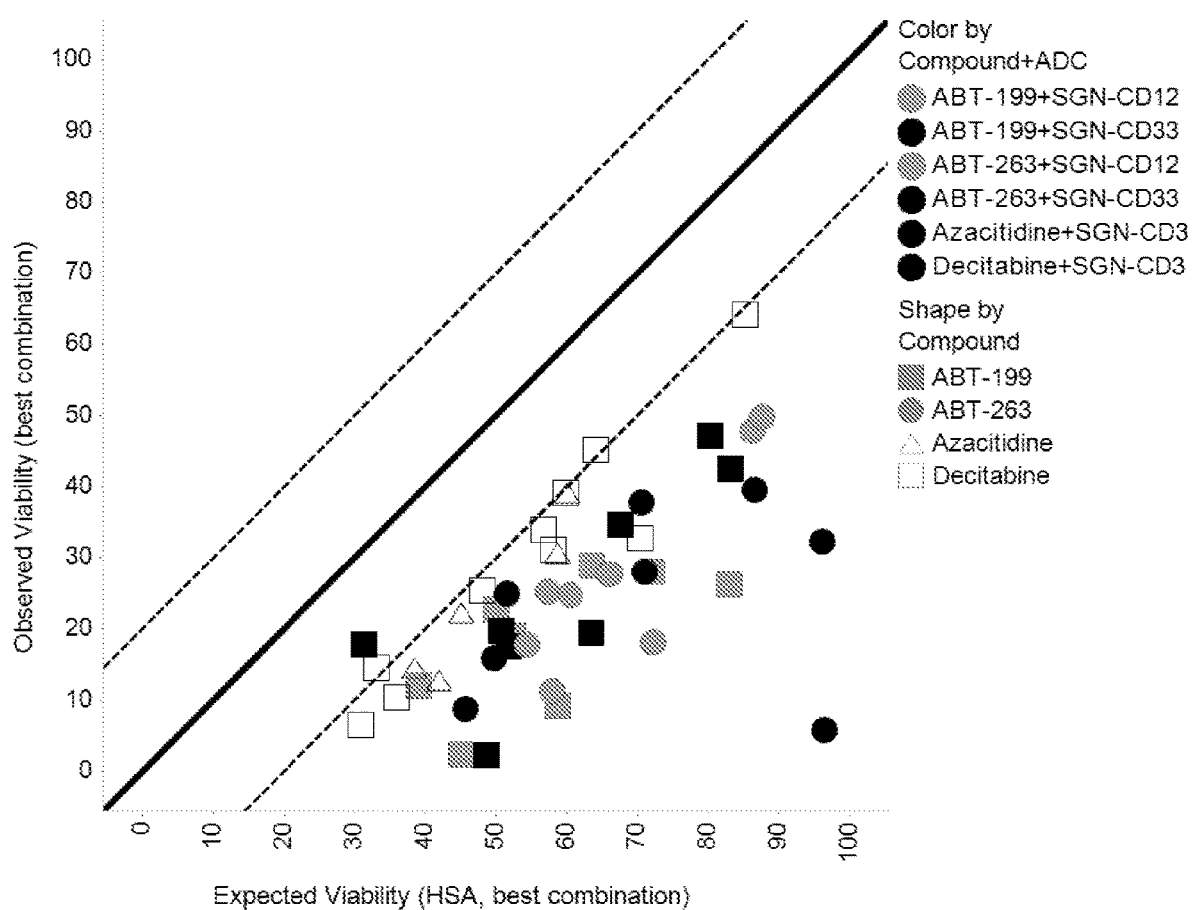
FIG. 1 shows observed versus expected viability for a CD33-ADC in combination with hypomethylating agents azacytidine or decitabine or with Bcl-2 inhibitors ABT-199 or ABT-263. The figure also shows observed versus expected viability for a CD123-ADC in combination with hypomethylating agents azacytidine or decitabine or with Bcl-2 inhibitors ABT-199 or ABT-263.

This disclosure demonstrates for the first time, that an ADC conjugated to a PBD, exhibits synergy when combined with a Bcl-2 inhibitor, e.g., ABT-199 or ABT-263.

I. Antibody Drug Conjugates

A. Antibodies

Antibodies that are part of antibody drug conjugates specifically bind to proteins that are expressed on cancer cells. In preferred embodiments, the proteins or epitopes bound by the antibodies are expressed on the external part of the cancer cell, e.g. are an external part of a transmembrane protein or are attached to the cell through a glycolipid anchor. The proteins bound by the antibody component of an ADC are preferably not expressed in non-cancerous cells or tissues or are expressed at higher levels in cancerous cells or tissues as compared to non-cancerous cells or tissues. Antibodies include, e.g., Fv, single-chain Fv (scFv), Fab, Fab', F(ab')2, F(ab)c, diabodies, dAbs, minibodies, nanobodies, Fab-scFv fusions, bispecific (scFv)4-IgG, and bispecific (scFv)2-Fab. In some aspects, the cysteine residue is substituted for serine in the antibody at position 239 (IgG1) as determined by the EU index (Kabat, *Sequences of Proteins of Immunological Interest* (National Institutes of Health, Bethesda, Md., 1987 and 1991). This cysteine substitution is referred to herein as S239C.

a. Anti-CD33 Antibodies

The anti-CD33 antibody disclosed herein is the humanized 2H12 antibody (h2H12). The murine 2H12 antibody was raised in mice, using the human CD33 protein as an immunogen. After making hybridomas from the spleens of the immunized mice, followed by screening for CD33 binding activity, the murine 2H12 antibody was selected for humanization. The h2H12 antibody was derived from the murine 2H12 antibody. The humanization procedure is disclosed in PCT publication WO 2013/173,496; which is herein incorporated by reference for all purposes. The variable region sequences of the h2H12 light and heavy chains are provided as SEQ ID NO:1 and SEQ ID NO:2, respectively.

The h2H12 antibody comprises human constant regions. Sequences of human constant regions are provided in the sequence listing. The heavy chain constant region of h2H12 includes a substitution mutation, S239C (numbering EU index according to Kabat), to facilitate conjugation of a drug-linker to the antibody. The sequence of a human constant region comprising the S239C mutation is provided at SEQ ID NOs:6 and 7. The h2H12 antibody comprising the S239C mutation is also referred to as h2H12EC.

b. Anti-CD123 Antibodies

The anti-CD123 antibody disclosed herein is the humanized 7G3 antibody (h7G3). The h7G3 antibody binds to the human CD123 protein was derived from the murine 7G3 antibody. The humanization procedure is disclosed in U.S. Ser. No. 62/175,121; which is herein incorporated by reference for all purposes. The variable region sequences of the h7G3 heavy and light chains are provided as SEQ ID NO:8 and SEQ ID NO:9, respectively.

The h7G3 antibody comprises human constant regions. Sequences of human constant regions are provided in the sequence listing. The heavy chain constant region of h7G3 includes a substitution mutation, S239C (numbering EU index according to Kabat), to facilitate conjugation of a drug-linker to the antibody. The sequence of a human constant region comprising the S239C mutation is provided at SEQ ID NOs:6 and 7. The h7G3 antibody comprising the S239C mutation is also referred to as h7G3EC.

c. Anti-CD19 Antibodies

The anti-CD19 antibody disclosed herein is the humanized BU12 antibody (hBU12). The hBU12 antibody binds to the human CD19 protein and was derived from the murine BU12 antibody. The humanization procedure is disclosed in WO2009/052431; which is herein incorporated by reference for all purposes. The variable region sequences of the hBU12 light and heavy chains are provided as SEQ ID NO:10 and SEQ ID NO:11, respectively.

The hBU12 antibody comprises human constant regions. Sequences of human constant regions are provided in the sequence listing. The heavy chain constant region of hBU12 includes a substitution mutation, S239C (numbering of EU index according to Kabat), to facilitate conjugation of a drug-linker to the antibody. The sequence of a human constant region comprising the S239C mutation is provided at SEQ ID NOs:6 and 7. The hBU12 antibody comprising the S239C mutation is also referred to as hBU12EC.

d. Anti-CD70 Antibodies

The anti-CD70 antibody disclosed herein is the humanized 1F6 antibody (h1F6). The h1F6 antibody binds to the human CD70 protein and was derived from the murine 1F6 antibody. The humanization procedure is disclosed in WO2006/113909; which is herein incorporated by reference for all purposes. The variable region sequences of the h1F6 light and heavy chains are provided as SEQ ID NO:12 and SEQ ID NO:13, respectively.

The h1F6 antibody comprises human constant regions. Sequences of human constant regions are provided in the sequence listing. The heavy chain constant region of h1F6 includes a substitution mutation, S239C (numbering of EU index according to Kabat), to facilitate conjugation of a drug-linker to the antibody. The sequence of a human constant region comprising the S239C mutation is provided at SEQ ID NOs:6 and 7. The h1F6 antibody comprising the S239C mutation is also referred to as h1F6EC.

e. Anti-CD352 Antibodies

The anti-CD352 antibody disclosed herein is the humanized 20F3 antibody (h20F3). The h20F3 antibody binds to the human CD70 protein and was derived from the murine 20F3 antibody. The humanization procedure is disclosed in U.S. Ser. No. 62/186,596 and U.S. Ser. No. 62/321,849; which are herein incorporated by reference for all purposes. The variable region sequences of the h20F3 light and heavy chains are provided as SEQ ID NO:14 and SEQ ID NO:15, respectively.

The h20F3 antibody comprises human constant regions. Sequences of human constant regions are provided in the sequence listing. The heavy chain constant region of h20F3 includes a substitution mutation, S239C (numbering of EU index according to Kabat), to facilitate conjugation of a drug-linker to the antibody. The sequence of a human constant region comprising the S239C mutation is provided at SEQ ID NOs:6 and 7. The h20F3 antibody comprising the S239C mutation is also referred to as h20F3EC.

B. Drug Linkers

Exemplary CD33 antibody-drug conjugates include PBD based antibody-drug conjugates; i.e., antibody-drug conjugates wherein the drug component is a PBD drug.

PBDs are of the general structure:

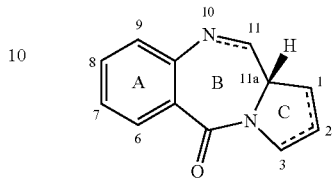

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position, which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, *In Antibiotics III*. Springer-Verlag, New York, pp. 3-11 (1975); Hurley and Needham-VanDevanter, *Acc. Chem. Res.*, 19, 230-237 (1986)). The ability of PBDs to form an adduct in the minor groove enables them to interfere with DNA processing, hence their use as antitumour agents.

The biological activity of these molecules can be potentiated by joining two PBD units together through their C8/C'-hydroxyl functionalities via a flexible alkylene linker (Bose, D. S., et al., *J. Am. Chem. Soc.*, 114, 4939-4941 (1992); Thurston, D. E., et al., *J. Org. Chem.*, 61, 8141-8147 (1996)). The PBD dimers are thought to form sequence-selective DNA lesions such as the palindromic 5'-Pu-GATC-Py-3' interstrand cross-link (Smellie, M., et al., *Biochemistry*, 42, 8232-8239 (2003); Martin, C., et al., *Biochemistry*, 44, 4135-4147) which is thought to be mainly responsible for their biological activity.

In some embodiments, PBD based antibody-drug conjugates comprise a PBD dimer linked to an anti-CD33 antibody. The monomers that form the PBD dimer can be the same or different, i.e., symmetrical or unsymmetrical. The PBD dimer can be linked to the anti-CD33 antibody at any position suitable for conjugation to a linker. For example, in some embodiments, the PBD dimer will have a substituent at the C2 position that provides an anchor for linking the compound to an antibody. In alternative embodiments, the N10 position of the PBD dimer will provide the anchor for linking the compound to an antibody.

Typically the PBD based antibody-drug conjugate comprises a linker between the PBD drug and an antibody. The linker may comprise a cleavable unit (e.g., an amino acid or a contiguous sequence of amino acids that is a target substrate for an enzyme) or a non-cleavable linker (e.g., linker released by degradation of the antibody). The linker may further comprise a maleimide group for linkage to the antibody, e.g., maleimidocaproyl. The linker may, in some embodiments, further comprise a self-immolative group, such as, for example, a p-aminobenzyl alcohol (PAB) unit.

An exemplary PBD for use as a conjugate is described in International Application No. WO 2011/130613 and is as follows wherein the wavy line indicates the site of attachment to the linker:

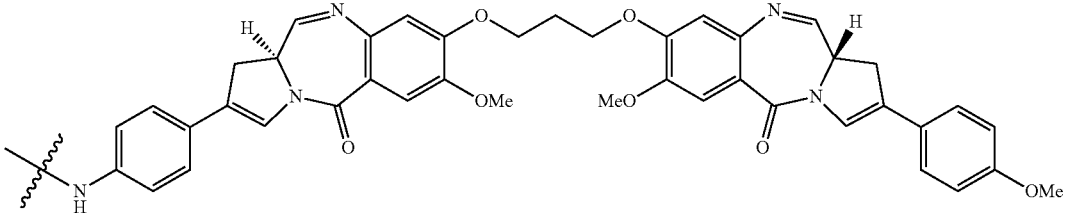

Formula I or a pharmaceutically acceptable salt thereof. An exemplary linker is as follows wherein the wavy line indicates the site of attachment to the drug and the antibody is linked via the maleimide group.

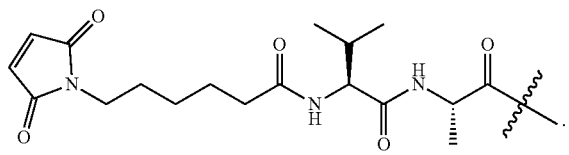

Formula 2

Exemplary PBDs based antibody-drug conjugates include antibody-drug conjugates as shown below wherein Ab is an antibody as described herein:

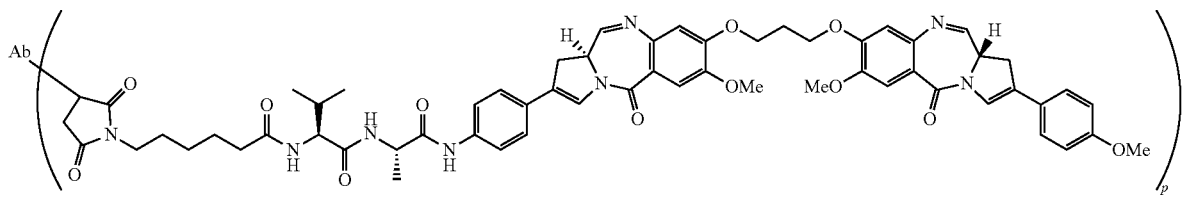

Formula 3 or a pharmaceutically acceptable salt thereof. The drug loading is represented by p, the number of drug-linker molecules per antibody. Depending on the context, p can represent the average number of drug-linker molecules per antibody, also referred to the average drug loading. The variable p ranges from 1 to 20 and is preferably from 1 to 8. In some preferred embodiments, when p represents the average drug loading, p ranges from about 2 to about 5. In some embodiments, p is about 2, about 3, about 4, or about 5. In some aspects, the antibody is conjugated to the drug linker via a sulfur atom of a cysteine residue that is engineered into the antibody. In some aspects, the cysteine residue is engineered into the antibody at position 239 (IgG1) as determined by the EU index (Kabat, *Sequences of Proteins of Immunological Interest* (National Institutes of Health, Bethesda, Md., 1987 and 1991).

C. Conjugation of Drug-Linkers to Antibodies

Antibody drug conjugates (ADCs) are formed by conjugation of a therapeutic antibody to a drug linker as described herein. The therapeutic antibody is selected by one of skill for its ability to bind specifically to a protein expressed on the external surface of a cancer cell. Preferably, the protein is differentially expressed on cancer cells, i.e., the protein is expressed at higher levels on cancer cells as compared to normal cells in the subject to be treated with the combination of an ADC and a Bcl-2 inhibitor.

Examples of therapeutic antibodies that can form the basis of an ADC include, e.g., anti-CD33 antibodies, such as h2H12 comprising heavy chain variable region SEQ ID NO:2 and light chain variable region SEQ ID NO:1; anti-CD123 antibodies, such as h7G3 comprising heavy chain variable region SEQ ID NO:8 and light chain variable region SEQ ID NO:9; anti-CD19 antibodies, such as hBU12 comprising heavy chain variable region SEQ ID NO:11 and light chain variable region SEQ ID NO:10; and anti-CD70 antibodies, such as h1F6 comprising heavy chain variable region SEQ ID NO:13 and light chain variable region SEQ ID NO:12.

In some embodiments, the antibody of the ADC includes an antibody constant region with a mutation in the heavy chain to facilitate conjugation of a PBD molecule to the antibody. The constant region is a preferably a human IgG1 constant region. In some embodiments, the heavy chain constant region has a substitution mutation at amino acid 239 using the EU index according to Kabat, i.e., referred to herein as S239C. The cysteine residue at position 239 is the point of attachment for the PBD molecule. The structure of the antibody, the linker and the PBD molecule is shown in Formula 3. Methods to make the PBD conjugated ADCs are disclosed in PCT publication WO 2011/130613, which is incorporated by reference for all purposes.

II. Bcl-2 Inhibitors

The term "Bcl-2" as used herein refers to the Bcl-2 protein (Swiss Prot ID No. P10415), a member of the Bcl-2 family of proteins (Cory, S., and Adams, J. M., *Nature Reviews Cancer* 2 (2002) 647-656; Adams, *Genes and Development* 17 (2003) 2481-2495; Danial, N. N., and Korsmeyer. S. J., *Cell* 116 (2004) 205-219; Petros. A. M., *Biochim Biophys Acta* 1644 (2004) 83-94).

The term "Bcl-2 inhibitors" as used herein refers to, e.g., 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-(((tetrahydro-2H-pyran-4-yl)methyl) amino)phenylsulfonyl)benzamide, (a.k.a. ABT-199, GDC-0199, RG7601, or venetoclax), which is described in International Publication No. WO2010/138588 and in US publication NO. US2010/0305122, which are incorporated by reference herein. Another Bcl-2 inhibitor is 4-(4-{[2-(4-Chlorophenyl)-5,5-dimethyl-1-cyclohexen-1-yl]methyl}-1-piperazinyl)-N-[(4-{[(2R)-4-(4-morpholinyl)-1-(phenylsulfanyl)-2-butanyl]amino}-3-[(trifluoromethyl)sulfonyl] phenyl)sulfonyl]benzamide, (a.k.a. ABT-263 or Navitoclax, CAS 923564-51-6, which is described in PCT Publication No. WO 09/155386. Other Bcl-2 inhibitors that may be used in the methods described herein include, e.g., Tetrocarcin A; Antimycin; Gossypol ((−)BL-193); ABT-737; Obatoclax; Ethyl-2-amino-6-cyclopentyl-4-(1-cyano-2-ethoxy-2-oxoethyl)-4Hchromone-3-carboxylate (HA14-1); Oblimersen (G3139, Genasense®); Bak BH3 peptide; (−)-Gossypol acetic acid (AT-101); and 4-[4-[(4'-Chloro[1,1'-biphenyl]-2-yl) methyl]-1-piperazinyl]-N-[[4-[[(1R)-3-(dimethylamino)-1 [(phenylthio)methyl]propyl]amino]-3-nitrophenyl] sulfonyl]-benzamide (ABT-737, CAS 852808-04-9).

III. Cancers that can be Treated Using Combinations of PBD-ADCs and Bcl-2 Inhibitors Cancers that can be treated using combinations of PBD-ADCs and Bcl-2 inhibitors are cancers that express antigens that are specifically bound by the antibody portion of the ADC. Exemplary cancers are cancers that express cancer-specific antigens, e.g., CD33, CD123, CD19, and CD70.

CD33 positive cancers can be treated using a combination of a CD33-binding ADC and a Bcl-2 inhibitor. CD33-expressing cancers show detectable levels of CD33 measured at either the protein (e.g., by immunoassay using one of the exemplified antibodies) or mRNA level. Some such cancers show elevated levels of CD33 relative to noncancerous tissue of the same type, preferably from the same patient. An exemplary level of CD33 on cancer cells amenable to treatment is 5000-150000 CD33 molecules per cell, although higher or lower levels can be treated. Optionally, a level of CD33 in a cancer is measured before performing treatment.

For example, an ADC that includes an antibody that specifically binds to the human CD33 protein can be used in combination with a Bcl-2 inhibitor to treat a human subject who has a cancer that expresses that CD33 protein. Such cancers include, e.g., myeloid diseases such as, acute myeloid leukemia (AML), chronic myeloid leukemia (CML), other myeloproliferative disorders, including chronic myelomonocytic leukemia and chronic myeloproliferative disorders, acute promyelocytic leukemia (APL), thrombocytic leukemia, a myelodysplastic syndrome, precursor B-cell acute lymphoblastic leukemia (preB-ALL), precursor T-cell acute lymphoblastic leukemia (preT-ALL), multiple myeloma (MM), mast cell disease including mast cell leukemia and mast cell sarcoma, myeloid sarcomas, refractory anemia, a preleukemia syndrome, a lymphoid leukemia, or an undifferentiated leukemia. The treatment can also be applied to patients who are treatment naïve, who are refractory to conventional treatments (e.g., chemotherapy or MYLOTARG® (gemtuzumab ozogamicin), or who have relapsed following a response to such treatments.

A combination of a CD33-ADC and a Bcl-2 inhibitor can be used to treat cancers that express CD33 protein. In one embodiment, a subject with a CD33 expressing cancer is treated with a combination of an ADC comprising the h2H12 antibody conjugated to a PBD-drug linker of formula 3 and a Bcl-2 inhibitor selected from ABT-199 or ABT-263. In another embodiment, a subject with a CD33 expressing cancer is treated with a combination of an ADC comprising the h2H12 antibody conjugated to a PBD-drug linker of formula 3 and the Bcl-2 inhibitor ABT-199. In another embodiment, a subject with a CD33 expressing cancer is treated with a combination of an ADC comprising the h2H12 antibody conjugated to a PBD-drug linker of formula 3 and the Bcl-2 inhibitor ABT-263. The CD33 expressing cancer for treatment with a CD33-ADC and a Bcl-2 inhibitor is selected from, e.g., CD33-positive acute myeloid leukemia (AML), CD33-positive chronic myeloid leukemia (CML), CD33-positive chronic myelomonocytic leukemia (CMML), CD33-positive thyroid leukemia, CD33-positive myelodysplastic syndrome, CD33-positive myeloproliferative disorder, CD33-positive refractory anemia, CD33-positive preleukemia syndrome, CD33-positive lymphoid leukemia, CD33-positive undifferentiated leukemia, CD33-positive precursor B-cell acute lymphoblastic leukemia (preB-ALL), CD33-positive precursor T-cell acute lymphoblastic leukemia (preT-ALL), CD33-positive multiple myeloma (MM) and CD33-positive mast cell disease including mast cell leukemia and mast cell sarcoma.

In one embodiment, a subject with CD33-positive acute myeloid leukemia (AML), is treated with a combination of an ADC comprising the h2H12 antibody conjugated to a PBD-drug linker depicted in formula 3 and a Bcl-2 inhibitor selected from ABT-199 or ABT-263. In another embodiment, a subject with CD33-positive AML is treated with a combination of an ADC comprising the h2H12 antibody conjugated to a PBD-drug linker of formula 3 and the Bcl-2 inhibitor ABT-199. In another embodiment, a subject with CD33-positive AML is treated with a combination of an ADC comprising the h2H12 antibody conjugated to a PBD-drug linker of formula 3 and the Bcl-2 inhibitor ABT-263.

CD123 positive cancers can be treated using a combination of a CD123-binding ADC and a Bcl-2 inhibitor. CD123-expressing cancers show detectable levels of CD123 measured at either the protein (e.g., by immunoassay using one of the exemplified antibodies) or mRNA level. Some such cancers show elevated levels of CD123 relative to noncancerous tissue of the same type, preferably from the same patient. An exemplary level of CD123 on cancer cells amenable to treatment is 5000-150000 CD123 molecules per cell, although higher or lower levels can be treated. Optionally, a level of CD123 in a cancer is measured before performing treatment.

For example, an ADC that includes an antibody that specifically binds to the human CD123 protein can be used in combination with a Bcl-2 inhibitor to treat a human subject who has a cancer that expresses that CD123 protein. Such cancers include, e.g., myeloid diseases such as, acute myeloid leukemia (AML) and myelodysplastic syndrome (MDS). Other cancers include B-cell acute lymphoblastic leukemia (B-ALL), hairy cell leukemia, Fanconi anemia, Blastic plasmacytoid dendritic cell neoplasm (BPDCN), Hodgkin's disease, Immature T-cell acute lymphoblastic leukemia (Immature T-ALL), Burkitt's lymphoma, Follicular lymphoma, chronic lymphocytic leukemia (CLL), or mantle cell lymphoma.

A combination of a CD123-ADC and a Bcl-2 inhibitor can be used to treat cancers that express CD123 protein. In one embodiment, a subject with a CD123 positive cancer is treated with a combination of an ADC comprising the h7G3 antibody conjugated to a PBD-drug linker of formula 3 and a Bcl-2 inhibitor selected from ABT-199 or ABT-263. In another embodiment, a subject with a CD123 expressing cancer is treated with a combination of an ADC comprising the h7G3 antibody conjugated to a PBD-drug linker of formula 3 and the Bcl-2 inhibitor ABT-199. In another embodiment, a subject with a CD123 expressing cancer is treated with a combination of an ADC comprising the h7G3 antibody conjugated to a PBD-drug linker of formula 3 and the Bcl-2 inhibitor ABT-263. The CD123 expressing cancer for treatment with a CD123-ADC and a Bcl-2 inhibitor is selected from, e.g., acute myeloid leukemia (AML) and myelodysplastic syndrome (MDS), B-cell acute lymphoblastic leukemia (B-ALL), hairy cell leukemia, Fanconi anemia, Blastic plasmacytoid dendritic cell neoplasm (BPDCN), Hodgkin's disease, Immature T-cell acute lymphoblastic leukemia (Immature T-ALL), Burkitt's lymphoma, Follicular lymphoma, chronic lymphocytic leukemia (CLL), or mantle cell lymphoma.

In one embodiment, a subject with CD123-positive acute myeloid leukemia (AML), is treated with a combination of an ADC comprising the h7G3 antibody conjugated to a PBD-drug linker of formula 3 and a Bcl-2 inhibitor selected from ABT-199 or ABT-263. In another embodiment, a subject with CD123-positive AML is treated with a combination of an ADC comprising the h7G3 antibody conjugated to a PBD-drug linker of formula 3 and the Bcl-2 inhibitor ABT-199. In another embodiment, a subject with CD123-positive AML is treated with a combination of an ADC comprising the h7G3 antibody conjugated to a PBD-drug linker of formula 3 and the Bcl-2 inhibitor ABT-263.

CD19 positive cancers can be treated using a combination of a CD19-binding ADC and a Bcl-2 inhibitor. CD19-expressing cancers show detectable levels of CD19 measured at either the protein (e.g., by immunoassay using one of the exemplified antibodies) or mRNA level. Some such cancers show elevated levels of CD19 relative to noncancerous tissue of the same type, preferably from the same patient. An exemplary level of CD19 on cancer cells amenable to treatment is 5000-150000 CD19 molecules per cell, although higher or lower levels can be treated. Optionally, a level of CD19 in a cancer is measured before performing treatment.

For example, an ADC that includes an antibody that specifically binds to the human CD19 protein can be used in combination with a Bcl-2 inhibitor to treat a human subject who has a cancer that expresses that CD19 protein. Such cancers include, e.g., B cell malignancies, for example, leukemias and lymphomas, including, but not limited to, B cell subtype non-Hodgkin's lymphoma (NHL) including low grade/follicular NHL, small lymphocytic (SL) NHL, intermediate grade/follicular NHL, intermediate grade diffuse NHL, diffuse large B-cell lymphoma, follicular lymphoma, high grade immunoblastic NHL, high grade lymphoblastic NHL, high grade small non-cleaved cell NHL, mantle cell lymphoma, and bulky disease NHL; Burkitt's lymphoma; multiple myeloma; pre-B acute lymphoblastic leukemia and other malignancies that derive from early B cell precursors; common acute lymphoblastic leukemia; chronic lymphocytic leukemia (CLL); hairy cell leukemia; Null-acute lymphoblastic leukemia; Waldenstrom's Macroglobulinemia; and pro-lymphocytic leukemia; diffuse large B cell lymphoma, pro-lymphocytic leukemia, light chain disease; plasmacytoma; osteosclerotic myeloma; plasma cell leukemia; monoclonal gammopathy of undetermined significance (MGUS); smoldering multiple myeloma (SMM); indolent multiple myeloma (IMM); or Hodgkin's lymphoma, provided that the cancers express the CD19 antigen.

A combination of a CD19-ADC and a Bcl-2 inhibitor can be used to treat cancers that express CD19 protein. In one embodiment, a subject with a CD19 positive cancer is treated with a combination of an ADC comprising the hBU12 antibody conjugated to a PBD-drug linker of formula 3 and a Bcl-2 inhibitor selected from ABT-199 or ABT-263. In another embodiment, a subject with a CD19 expressing cancer is treated with a combination of an ADC comprising the hBU12 antibody conjugated to a PBD-drug linker of formula 3 and the Bcl-2 inhibitor ABT-199. In another embodiment, a subject with a CD19 expressing cancer is treated with a combination of an ADC comprising the hBU12 antibody conjugated to a PBD-drug linker of formula 3 and the Bcl-2 inhibitor ABT-263. The CD19 expressing cancer for treatment with a CD19-ADC and a Bcl-2 inhibitor is selected from, e.g., B cell malignancies, including, for example, leukemias and lymphomas, including, but not limited to, B cell subtype non-Hodgkin's lymphoma (NHL) including low grade/follicular NHL, small lymphocytic (SL) NHL, intermediate grade/follicular NHL, intermediate grade diffuse NHL, diffuse large B-cell lymphoma, follicular lymphoma, high grade immunoblastic NHL, high grade lymphoblastic NHL, high grade small non-cleaved cell NHL, mantle cell lymphoma, and bulky disease NHL; Burkitt's lymphoma; multiple myeloma; pre-B acute lymphoblastic leukemia and other malignancies that derive from early B cell precursors; common acute lymphoblastic leukemia; chronic lymphocytic leukemia; hairy cell leukemia; Null-acute lymphoblastic leukemia; Waldenstrom's Macroglobulinemia; and pro-lymphocytic leukemia; diffuse large B cell lymphoma, pro-lymphocytic leukemia, light chain disease; plasmacytoma; osteosclerotic myeloma; plasma cell leukemia; monoclonal gammopathy of undetermined significance (MGUS); smoldering multiple myeloma (SMM); indolent multiple myeloma (IMM); or Hodgkin's lymphoma, provided that the cancers express the CD19 antigen.

In one embodiment, a subject with CD19-positive non-hodgkins lymphoma (NHL) is treated with a combination of an ADC comprising the hBU12 antibody conjugated to a PBD-drug linker of formula 3 and a Bcl-2 inhibitor selected from ABT-199 or ABT-263. In another embodiment, a subject with CD19-positive NHL is treated with a combination of an ADC comprising the hBU12 antibody conjugated to a PBD-drug linker of formula 3 and the Bcl-2 inhibitor ABT-199. In another embodiment, a subject with CD19-positive NHL is treated with a combination of an ADC comprising the hBU12 antibody conjugated to a PBD-drug linker of formula 3 and the Bcl-2 inhibitor ABT-263.

In one embodiment, a subject with CD19-positive acute lymphoblastic leukemia (ALL) is treated with a combination of an ADC comprising the hBU12 antibody conjugated to a PBD-drug linker of formula 3 and a Bcl-2 inhibitor selected from ABT-199 or ABT-263. In another embodiment, a subject with CD19-positive ALL is treated with a combination of an ADC comprising the hBU12 antibody conjugated to a PBD-drug linker of formula 3 and the Bcl-2 inhibitor ABT-199. In another embodiment, a subject with CD19-positive ALL is treated with a combination of an ADC comprising the hBU12 antibody conjugated to a PBD-drug linker of formula 3 and the Bcl-2 inhibitor ABT-263.

In one embodiment, a subject with CD19-positive hodgkins lymphoma is treated with a combination of an ADC comprising the hBU12 antibody conjugated to a PBD-drug linker of formula 3 and a Bcl-2 inhibitor selected from ABT-199 or ABT-263. In another embodiment, a subject with CD19-positive hodgkins lymphoma is treated with a combination of an ADC comprising the hBU12 antibody conjugated to a PBD-drug linker of formula 3 and the Bcl-2 inhibitor ABT-199. In another embodiment, a subject with CD19-positive hodgkins lymphoma is treated with a combination of an ADC comprising the hBU12 antibody conjugated to a PBD-drug linker of formula 3 and the Bcl-2 inhibitor ABT-263.

In one embodiment, a subject with CD19-positive chronic lymphocytic leukemia (CLL) is treated with a combination of an ADC comprising the hBU12 antibody conjugated to a PBD-drug linker of formula 3 and a Bcl-2 inhibitor selected from ABT-199 or ABT-263. In another embodiment, a subject with CD19-positive CLL is treated with a combination of an ADC comprising the hBU12 antibody conjugated to a PBD-drug linker of formula 3 and the Bcl-2 inhibitor ABT-199. In another embodiment, a subject with CD19-positive CLL is treated with a combination of an ADC comprising the hBU12 antibody conjugated to a PBD-drug linker of formula 3 and the Bcl-2 inhibitor ABT-263.

CD70 positive cancers can be treated using a combination of a CD70-binding ADC and a Bcl-2 inhibitor. CD70-expressing cancers show detectable levels of CD70 measured at either the protein (e.g., by immunoassay using one of the exemplified antibodies) or mRNA level. Some such cancers show elevated levels of CD70 relative to noncancerous tissue of the same type, preferably from the same patient. An exemplary level of CD70 on cancer cells amenable to treatment is 5000-150000 CD70 molecules per cell, although higher or lower levels can be treated. Optionally, a level of CD70 in a cancer is measured before performing treatment.

For example, an ADC that includes an antibody that specifically binds to the human CD70 protein can be used in combination with a Bcl-2 inhibitor to treat a human subject who has a cancer that expresses that CD70 protein. Such cancers include, Non-Hodgkin's Lymphoma (NHL), including NHL subtypes such as indolent NHLs, follicular NHLs, small lymphocytic lymphomas, lymphoplasmacytic NHLs, or marginal zone NHLs; Hodgkin's disease (e.g., Reed-Sternberg cells); cancers of the B-cell lineage, including, e.g., diffuse large B-cell lymphomas, follicular lymphomas, Burkitt's lymphoma, mantle cell lymphomas, B-cell lymphocytic leukemias (e.g., acute lymphocytic leukemia, chronic lymphocytic leukemia); Epstein Barr Virus positive B cell lymphomas; renal cell carcinomas (e.g., clear cell and papillary); nasopharyngeal carcinomas; thymic carcinomas; gliomas; glioblastomas; neuroblastomas; astrocytomas; meningiomas; Waldenstrom macroglobulinemia; multiple myelomas; and colon, stomach, and rectal carcinomas.

A combination of a CD70-ADC and a Bcl-2 inhibitor can be used to treat cancers that express CD70 protein. In one embodiment, a subject with a CD70 positive cancer is treated with a combination of an ADC comprising the h1F6 antibody conjugated to a PBD-drug linker of formula 3 and a Bcl-2 inhibitor selected from ABT-199 or ABT-263. In another embodiment, a subject with a CD70 expressing cancer is treated with a combination of an ADC comprising the h1F6 antibody conjugated to a PBD-drug linker of formula 3 and the Bcl-2 inhibitor ABT-199. In another embodiment, a subject with a CD70 expressing cancer is treated with a combination of an ADC comprising the h1F6 antibody conjugated to a PBD-drug linker of formula 3 and the Bcl-2 inhibitor ABT-263. The CD70 expressing cancer for treatment with a CD70-ADC and a Bcl-2 inhibitor is selected from, e.g., Non-Hodgkin's Lymphoma (NHL), including NHL subtypes such as indolent NHLs, follicular NHLs, small lymphocytic lymphomas, lymphoplasmacytic NHLs, or marginal zone NHLs; Hodgkin's disease (e.g., Reed-Sternberg cells); cancers of the B-cell lineage, including, e.g., diffuse large B-cell lymphomas, follicular lymphomas, Burkitt's lymphoma, mantle cell lymphomas, B-cell lymphocytic leukemias (e.g., acute lymphocytic leukemia, chronic lymphocytic leukemia); Epstein Barr Virus positive B cell lymphomas; renal cell carcinomas (e.g., clear cell and papillary); nasopharyngeal carcinomas; thymic carcinomas; gliomas; glioblastomas; neuroblastomas; astrocytomas; meningiomas; Waldenstrom macroglobulinemia; multiple myelomas; and colon, stomach, and rectal carcinomas.

In one embodiment, a subject with CD70-positive non-hodgkins lymphoma (NHL) is treated with a combination of an ADC comprising the h1F6 antibody conjugated to a PBD-drug linker of formula 3 and a Bcl-2 inhibitor selected from ABT-199 or ABT-263. In another embodiment, a subject with CD70-positive NHL is treated with a combination of an ADC comprising the h1F6 antibody conjugated to a PBD-drug linker of formula 3 and the Bcl-2 inhibitor ABT-199. In another embodiment, a subject with CD70-positive NHL is treated with a combination of an ADC comprising the h1F6 antibody conjugated to a PBD-drug linker of formula 3 and the Bcl-2 inhibitor ABT-263.

In one embodiment, a subject with CD70-positive renal cell carcinoma (RCC) is treated with a combination of an ADC comprising the h1F6 antibody conjugated to a PBD-drug linker of formula 3 and a Bcl-2 inhibitor selected from ABT-199 or ABT-263. In another embodiment, a subject with CD70-positive RCC is treated with a combination of an ADC comprising the h1F6 antibody conjugated to a PBD-drug linker of formula 3 and the Bcl-2 inhibitor ABT-199. In another embodiment, a subject with CD70-positive RCC is treated with a combination of an ADC comprising the h1F6 antibody conjugated to a PBD-drug linker of formula 3 and the Bcl-2 inhibitor ABT-263.

CD352 positive cancers can be treated using a combination of a CD352-binding ADC and a Bcl-2 inhibitor. CD352-expressing cancers show detectable levels of CD352 measured at either the protein (e.g., by immunoassay using one of the exemplified antibodies) or mRNA level. Some such cancers show elevated levels of CD352 relative to noncancerous tissue of the same type, preferably from the same patient. An exemplary level of CD352 on cancer cells amenable to treatment is 5000-150000 CD352 molecules per cell, although higher or lower levels can be treated. Optionally, a level of CD352 in a cancer is measured before performing treatment.

For example, an ADC that includes an antibody that specifically binds to the human CD352 protein can be used in combination with a Bcl-2 inhibitor to treat a human subject who has a cancer that expresses that CD352 protein. Such cancers include, e.g., hematological malignancies, including B-cell, T-cell, and NK-cell malignancies. In some methods of treatment, the patient has a cancer, which is a multiple myeloma, an acute myeloid leukemia (AML), a chronic lymphocytic leukemia (CLL), a T-Cell or B-cell lymphoma such as, e.g., a non-Hodgkin's lymphoma (NHL), or myeloma related malignancies such as primary amyloidosis, Waldenström's macroglobulinemia, or high risk MGUS (monoclonal gammopathy of undetermined significance).

A combination of a CD352-ADC and a Bcl-2 inhibitor can be used to treat cancers that express CD352 protein. In one embodiment, a subject with a CD352 positive cancer is treated with a combination of an ADC comprising the h20F3 antibody conjugated to a PBD-drug linker of formula 3 and a Bcl-2 inhibitor selected from ABT-199 or ABT-263. In another embodiment, a subject with a CD352 expressing cancer is treated with a combination of an ADC comprising the h20F antibody conjugated to a PBD-drug linker of formula 3 and the Bcl-2 inhibitor ABT-199. In another embodiment, a subject with a CD352 expressing cancer is treated with a combination of an ADC comprising the h20F3 antibody conjugated to a PBD-drug linker of formula 3 and the Bcl-2 inhibitor ABT-263. The CD352 expressing cancer for treatment with a CD352-ADC and a Bcl-2 inhibitor is selected from, e.g., a multiple myeloma, an acute myeloid leukemia (AML), a chronic lymphocytic leukemia (CLL), a T-Cell or B-cell lymphoma such as, e.g., a non-Hodgkin's lymphoma (NHL), or myeloma related malignancies such as primary amyloidosis, Waldenstrom's macroglobulinemia, or high risk MGUS (monoclonal gammopathy of undetermined significance).

In one embodiment, a subject with CD352-positive multiple myeloma (MM), is treated with a combination of an ADC comprising the h20F3 antibody conjugated to a PBD-drug linker of formula 3 and a Bcl-2 inhibitor selected from ABT-199 or ABT-263. In another embodiment, a subject with CD352-positive MM is treated with a combination of an ADC comprising the h20F3 antibody conjugated to a PBD-drug linker of formula 3 and the Bcl-2 inhibitor ABT-199. In another embodiment, a subject with CD352-positive MM is treated with a combination of an ADC comprising the h20F3 antibody conjugated to a PBD-drug linker of formula 3 and the Bcl-2 inhibitor ABT-263.

IV. Dosage and Administration

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use. Formulations for ADCs comprising antibodies and a PBD molecules are disclosed e.g., at PCT/US2014/024466.

The ADC is administered intravenously. Bcl-2 inhibitors are administered in an appropriate manner as directed by the manufacturer. For example, Bcl-2 inhibitors ABT-199 and ABT263 can be administered orally.

An ADC comprising an antibody that specifically binds a protein expressed by a cancer can be combined with a Bcl-2 inhibitor concurrently or sequentially for treatment of a cancer or disorder, at the discretion of the treating physician.

In one embodiment, the combination of an ADC with a Bcl-2 inhibitor is dosed on a twenty-eight day schedule. The Bcl-2 inhibitor is administered on days 7-14. In one embodiment, the ADC is administered on day 1 of the cycle. In one embodiment, the ADC is administered on the final day of Bcl-2 inhibitor treatment. In another embodiment, the ADC is administered one week after the final day of Bcl-2 inhibitor treatment. In other embodiments, the ADC dose is split, e.g., half the dose is administered on a specified day and a second half is administered later during the cycle. After day 28, the cycle is repeated, with the total number of cycles determined by the physician.

In one embodiment, the combination of an ADC with a Bcl-2 inhibitor is dosed on a twenty-one day schedule. The Bcl-2 inhibitor is administered on days 7-14. In one embodiment, the ADC is administered on day 1 of the cycle. In one embodiment, the ADC is administered on the final day of Bcl-2 inhibitor treatment. In another embodiment, the ADC is administered one week after the final day of Bcl-2 inhibitor treatment. In other embodiments, the ADC dose is split, e.g., half the dose is administered on a specified day and a second half is administered later during the cycle. After day 21, the cycle is repeated, with the total number of cycles determined by the physician.

The ADC can be administered in combination with a Bcl-2 inhibitor in the following dose ranges: 5-60 µg/kg, 5-40 µg/kg, 5-25 µg/kg, 10-30 µg/kg, 5-20 µg/kg, 5-15 µg/kg, or 5-10 µg/kg. In some embodiments, the ADC is administered at about 10 µg/kg in combination with a Bcl-2 inhibitor. In another embodiment, the ADC is administered at 10 µg/kg in combination with a Bcl-2 inhibitor. In other embodiments, the ADC is administered at 5 µg/kg, 6 µg/kg, 7 µg/kg, 8 µg/kg, 9 µg/kg, 10 µg/kg, 15 µg/kg, 20 µg/kg, 25 µg/kg, or 30 µg/kg in combination with a Bcl-2 inhibitor.

Bcl-2 inhibitors are adminstered in the following dosage ranges: 10-200 mg/m$^2$, 25-150 mg/m$^2$, or 50-100 mg/m$^2$. In some embodiments, Bcl-2 inhibitors are administered as a flat dose in combination with an ADC comprising a PBD molecule. For example, ventoclax (ABT-199) can be administered at ranges of 400-800 mg/day for days 7-14 of a 21-28 day cycle.

In one embodiment, an ADC comprising an antibody that specifically binds a CD33 protein expressed by a cancer cell can be combined with the Bcl-2 inhibitor ventoclax for treatment of a CD33-positive cancer. In a further embodiment, the ADC comprises the h2H12 antibody and is conjugated to a PBD molecule as shown in Formula 3. The h2H12 antibody comprises S239C mutations in the heavy chain constant region and the S239C residues are used for conjugation of the PBD molecule to the antibody.

In one embodiment, the combination of a CD33-specific ADC comprising the h2H12 antibody conjugated to a PBD molecule as in Formula 3 with ventoclax is dosed on a twenty-eight day schedule. Venetoclax is administered on days 7-14. In one embodiment, the CD33-specific ADC is administered on day 1 of the cycle. In one embodiment, the CD-33 specific ADC is administered on the final day of venetoclax treatment. In another embodiment, the Cd333-specific ADC is administered one week after the final day of venetoclax treatment. In other embodiments, the CD33-specificADC dose is split, e.g., half the dose is administered on a specified day and a second half is administered later during the cycle. After day 28, the cycle is repeated, with the total number of cycles determined by the physician.

In one embodiment, the combination of a CD33-specific ADC comprising the h2H12 antibody conjugated to a PBD molecule as in Formula 3 with ventoclax is dosed on a twenty-one day schedule. The venetoclax is administered on days 7-14. In one embodiment, the CD33-specific ADC is administered on day 1 of the cycle. In one embodiment, the CD-33 specific ADC is administered on the final day of venetoclax treatment. In another embodiment, the CD-33-specific ADC is administered one week after the final day of venetoclax treatment. In other embodiments, the CD33-specific ADC dose is split, e.g., half the dose is administered on a specified day and a second half is administered later during the cycle. After day 21, the cycle is repeated, with the total number of cycles determined by the physician.

The CD33-specific ADC, i.e., an ADC comprising the h2H12 antibody conjugated to a PBD molecule as in Formula 3, can be administered in combination with venetoclax in the following dose ranges: 5-60 µg/kg, 5-40 µg/kg, 5-25

µg/kg, 10-30 µg/kg, 5-20 µg/kg, 5-15 µg/kg, or 5-10 µg/kg. In some embodiments, the CD33-specific ADC is administered at about 10 µg/kg in combination with venetoclax. In another embodiment, the CD-33 specific ADC is administered at 10 µg/kg in combination with venetoclax. In other embodiments, the CD33-specific ADC is administered at 5 µg/kg, 6 µg/kg, 7 µg/kg, 8 µg/kg, 9 µg/kg, 10 µg/kg, 15 µg/kg, 20 µg/kg, 25 µg/kg, or 30 µg/kg in combination with venetoclax. Ventoclax (ABT-199) can be administered at ranges of 400-800 mg/day for days 7-14 of a 21-28 day cycle in combination with the CD33-specific ADC comprising the h2H12 antibody conjugated to a PBD molecule as in Formula 3.

In some embodiments, the combination of a PBD-containing ADC and a Bcl-2 inhibitor is administered to a patient that has a cancer that expresses high levels of Bcl-2 protein or exhibits high levels of Bcl-2 function. In other embodiments, the combination of a PBD-containing ADC and a Bcl-2 inhibitor is administered to a patient that has a cancer that expresses high levels of Bcl-2 protein as compared to the Bcl-xl protein and/or the Mcl-1 protein. The Bcl-2 inhibitor is preferably ABT-199.

Bcl-2 protein levels in tumor samples can be determined using methods known to those of skill in the art. The human Bcl-2 protein and mRNA sequences are known to those of skill, see, e.g., UniProtKB/Swiss-Prot: P10415.2 (protein) and NM_000633.2 (protein and mRNA). Since Bcl-2 antibodies are known and commercially available, Bcl-2 protein levels can be determined using methods known to those of skill in the art, e.g. ELISA, flow cytometry, immunohistochemistry, western blotting. Bcl-2 mRNA levels can be assessed using northern blots, quantitative PCR. These methods can also be used to determine protein and mRNA levels of Bcl-xl (protein accession number CAA80661.1; mRNA accession number GenBank: Z23115.1), as well as protein and mRNA levels of Mcl-1 (protein accession number NP_068779.1; mRNA accession number NM_021960.4).

The function of Bcl-2 and family members can also be assessed. For example, cells from tumors can be assessed for apoptotic activity in the presence of specific inhibitors, ABT-199 and ABT-263. The function of multiple Bcl family members, e.g., Bcl-2, Bcl-xl, and Mcl-1 can be assessed using a BH3 profiling test. See, e.g., Friedman et al., *Nat. Revs. Cancer,* 15:747-756 (2015). The likelihood of a cancer cell undergoing apoptosis can also be assessed by determining mitochondrial outer membrane permeabilization (MOMP). See, e.g., Chupik et al., *Cell Death and Diff.* 13:1396-1402 (2006). Assays for MOMP are known to those of skill. See, e.g., Renault et al., *Methods* 61:146-155 (2013).

In some embodiments, the function or expression of Bcl-2 and Bcl-xl are measured in in a cancer cell sample from a patient. A combination of a PBD-ADC and a Bcl-2 inhibitor is administered to the patient if the Bcl-2 level of expression or function exceeds the Bcl-xl level of expression or function by at least, e.g., 1.5-fold, 2-fold, 3-fold, 5-fold, or 10 fold. In one embodiment, combination of a CD33-ADC comprising a PBD and the Bcl-2 inhibitor ABT-199 is administered to a patient with CD33-positive AML if the Bcl-2 level of expression or function exceeds the Bcl-xl level of expression or function in an AML sample from the patient by at least, e.g., 1.5-fold, 2-fold, 3-fold, 5-fold, or 10 fold. In a further embodiment, the combination of a CD33-ADC comprising a PBD and the Bcl-2 inhibitor ABT-199 is administered to a patient with CD33-positive AML if the Bcl-2 level of expression or function exceeds the Bcl-xl level of expression or function in an AML sample from the patient by 2-fold.

In one embodiment, a combination of a CD33-ADC and a Bcl-2 inhibitor is used to treat cancers that express CD33 protein and that have high levels of Bcl-2 expression or function or that have a high level of Bcl-2 expression or function as compared to expression or function of Bcl-xl or Mcl-1. In one embodiment, a subject with a CD33 expressing cancer with high Bcl-2 expression or function is treated with a combination of an ADC comprising the h2H12 antibody conjugated to a PBD-drug linker of formula 3 and the Bcl-2 inhibitor ABT-199. The CD33 expressing cancer for treatment with a CD33-ADC and a Bcl-2 inhibitor is selected from, e.g., CD33-positive acute myeloid leukemia (AML), CD33-positive chronic myeloid leukemia (CML), CD33-positive chronic myelomonocytic leukemia (CMML), CD33-positive thyroid leukemia, CD33-positive myelodysplastic syndrome, CD33-positive myeloproliferative disorder, CD33-positive refractory anemia, CD33-positive preleukemia syndrome, CD33-positive lymphoid leukemia, CD33-positive undifferentiated leukemia, CD33-positive precursor B-cell acute lymphoblastic leukemia (preB-ALL), CD33-positive precursor T-cell acute lymphoblastic leukemia (preT-ALL), CD33-positive multiple myeloma (MM) and CD33-positive mast cell disease including mast cell leukemia and mast cell sarcoma.

In one embodiment, a subject with CD33-positive acute myeloid leukemia (AML) that has high Bcl-2 expression or function or that has a high level of Bcl-2 expression or function as compared to expression or function of Bcl-xl or Mcl-1, is treated with a combination of an ADC comprising the h2H12 antibody conjugated to a PBD-drug linker of formula 3 and the Bcl-2 inhibitor ABT-199.

In one embodiment, a combination of a CD123-ADC and a Bcl-2 inhibitor can be used to treat cancers that express CD123 protein and that have high levels of Bcl-2 expression or function or that have a high level of Bcl-2 expression or function as compared to expression or function of Bcl-xl or Mcl-1. In one embodiment, a subject with a CD123 expressing cancer with high Bcl-2 expression or function is treated with a combination of an ADC comprising the h7G3 antibody conjugated to a PBD-drug linker of formula 3 and the Bcl-2 inhibitor ABT-199. The CD123 expressing cancer for treatment with a CD123-ADC and a Bcl-2 inhibitor is selected from, e.g., acute myeloid leukemia (AML) and myelodysplastic syndrome (MDS), B-cell acute lymphoblastic leukemia (B-ALL), hairy cell leukemia, Fanconi anemia, Blastic plasmacytoid dendritic cell neoplasm (BPDCN), Hodgkin's disease, Immature T-cell acute lymphoblastic leukemia (Immature T-ALL), Burkitt's lymphoma, Follicular lymphoma, chronic lymphocytic leukemia (CLL), or mantle cell lymphoma.

In one embodiment, a subject with CD123-positive acute myeloid leukemia (AML) that has high Bcl-2 expression or function or that has a high level of Bcl-2 expression or function as compared to expression or function of Bcl-xl or Mcl-1, is treated with a combination of an ADC comprising the h7G3 antibody conjugated to a PBD-drug linker of formula 3 and the Bcl-2 inhibitor ABT-199.

In one embodiment, a combination of a CD19-ADC and a Bcl-2 inhibitor can be used to treat cancers that express CD19 protein and that have high levels of Bcl-2 expression or function or that have a high level of Bcl-2 expression or function as compared to expression or function of Bcl-xl or Mcl-1. In another embodiment, a subject with a CD19 expressing cancer with high Bcl-2 expression or function is treated with a combination of an ADC comprising the hBU12 antibody conjugated to a PBD-drug linker of formula 3 and the Bcl-2 inhibitor ABT-199. The CD19 expressing cancer with high Bcl-2 expression or function for treatment with a CD19-ADC and a Bcl-2 inhibitor is selected from, e.g., B cell malignancies, including, for example, leukemias and lymphomas, including, but not limited to, B cell subtype non-Hodgkin's lymphoma (NHL) including low grade/follicular NHL, small lymphocytic (SL) NHL, intermediate grade/follicular NHL, intermediate grade diffuse NHL, diffuse large B-cell lymphoma, follicular lymphoma, high grade immunoblastic NHL, high grade lymphoblastic NHL, high grade small non-cleaved cell NHL, mantle cell lymphoma, and bulky disease NHL; Burkitt's lymphoma; multiple myeloma; pre-B acute lymphoblastic leukemia and other malignancies that derive from early B cell precursors; common acute lymphoblastic leukemia; chronic lymphocytic leukemia; hairy cell leukemia; Null-acute lymphoblastic leukemia; Waldenstrom's Macroglobulinemia; and pro-lymphocytic leukemia; diffuse large B cell lymphoma, pro-lymphocytic leukemia, light chain disease; plasmacytoma; osteosclerotic myeloma; plasma cell leukemia; monoclonal gammopathy of undetermined significance (MGUS); smoldering multiple myeloma (SMM); indolent multiple myeloma (IMM); or Hodgkin's lymphoma, provided that the cancers express the CD19 antigen.

In one embodiment, a subject with CD19-positive non-hodgkins lymphoma (NHL) that has high Bcl-2 expression or function or that has a high level of Bcl-2 expression or function as compared to expression or function of Bcl-xl or Mcl-1, is treated with a combination of an ADC comprising the hBU12 antibody conjugated to a PBD-drug linker of formula 3 and the Bcl-2 inhibitor ABT-199.

In one embodiment, a subject with CD19-positive acute lymphoblastic leukemia (ALL) that has high Bcl-2 expression or function or that has a high level of Bcl-2 expression or function as compared to expression or function of Bcl-xl or Mcl-1, is treated with a combination of an ADC comprising the hBU12 antibody conjugated to a PBD-drug linker of formula 3 and the Bcl-2 inhibitor ABT-199.

In one embodiment, a subject with CD19-positive hodgkins lymphoma that has high Bcl-2 expression or function or that has a high level of Bcl-2 expression or function as compared to expression or function of Bcl-xl or Mcl-1, is treated with a combination of an ADC comprising the hBU12 antibody conjugated to a PBD-drug linker of formula 3 the Bcl-2 inhibitor ABT-199.

In one embodiment, a subject with CD19-positive chronic lymphocytic leukemia (CLL) that has high Bcl-2 expression or function or that has a high level of Bcl-2 expression or function as compared to expression or function of Bcl-xl or Mcl-1, is treated with a combination of an ADC comprising the hBU12 antibody conjugated to a PBD-drug linker of formula 3 and the Bcl-2 inhibitor ABT-199.

In one embodiment, a combination of a CD70-ADC and a Bcl-2 inhibitor can be used to treat cancers that express CD70 protein and that have high levels of Bcl-2 expression or function or that have a high level of Bcl-2 expression or function as compared to expression or function of Bcl-xl or Mcl-1. In one embodiment, a subject with a CD70 positive cancer that has high Bcl-2 expression or function is treated with a combination of an ADC comprising the h1F6 antibody conjugated to a PBD-drug linker of formula 3 and the Bcl-2 inhibitor ABT-199. The CD70 expressing cancer for treatment with a CD70-ADC and a Bcl-2 inhibitor is selected from, e.g., Non-Hodgkin's Lymphoma (NHL), including NHL subtypes such as indolent NHLs, follicular NHLs, small lymphocytic lymphomas, lymphoplasmacytic NHLs, or marginal zone NHLs; Hodgkin's disease (e.g., Reed-Sternberg cells); cancers of the B-cell lineage, including, e.g., diffuse large B-cell lymphomas, follicular lymphomas, Burkitt's lymphoma, mantle cell lymphomas, B-cell lymphocytic leukemias (e.g., acute lymphocytic leukemia, chronic lymphocytic leukemia); Epstein Barr Virus positive B cell lymphomas; renal cell carcinomas (e.g., clear cell and papillary); nasopharyngeal carcinomas; thymic carcinomas; gliomas; glioblastomas; neuroblastomas; astrocytomas; meningiomas; Waldenstrom macroglobulinemia; multiple myelomas; and colon, stomach, and rectal carcinomas.

In one embodiment, a subject with CD70-positive non-hodgkins lymphoma (NHL) that has high Bcl-2 expression or function or that has a high level of Bcl-2 expression or function as compared to expression or function of Bcl-xl or Mcl-1, is treated with a combination of an ADC comprising the h1F6 antibody conjugated to a PBD-drug linker of formula 3 and a the Bcl-2 inhibitor ABT-199.

In one embodiment, a subject with CD70-positive renal cell carcinoma (RCC) that has high Bcl-2 expression or function or that has a high level of Bcl-2 expression or function as compared to expression or function of Bcl-xl or Mcl-1, is treated with a combination of an ADC comprising the h1F6 antibody conjugated to a PBD-drug linker of formula 3 the Bcl-2 inhibitor ABT-199.

In one embodiment, a combination of a CD352-ADC and a Bcl-2 inhibitor can be used to treat cancers that express CD352 protein and that have high levels of Bcl-2 expression or function or that have a high level of Bcl-2 expression or function as compared to expression or function of Bcl-xl or Mcl-1. In another embodiment, a subject with a CD352 expressing cancer that has a high level of Bcl-2 expression or function is treated with a combination of an ADC comprising the h20F antibody conjugated to a PBD-drug linker of formula 3 and the Bcl-2 inhibitor ABT-199. The CD352 expressing cancer for treatment with a CD352-ADC and a Bcl-2 inhibitor is selected from, e.g., a multiple myeloma, an acute myeloid leukemia (AML), a chronic lymphocytic leukemia (CLL), a T-Cell or B-cell lymphoma such as, e.g., a non-Hodgkin's lymphoma (NHL), or myeloma related malignancies such as primary amyloidosis, Waldenström's macroglobulinemia, or high risk MGUS (monoclonal gammopathy of undetermined significance).

In one embodiment, a subject with CD352-positive multiple myeloma (MM) that has high Bcl-2 expression or function or that has a high level of Bcl-2 expression or function as compared to expression or function of Bcl-xl or Mcl-1, is treated with a combination of an ADC comprising the h20F3 antibody conjugated to a PBD-drug linker of formula 3 and the Bcl-2 inhibitor ABT-199.

EXAMPLES

The following examples are offered to illustrate, but not to limit the claimed invention.

Example 1: ADC's Comprising PBDs Exhibit Synergism in Combination with Bcl-2 Inhibitors Methods
In Vitro Cytotoxicity Assay For assessment of Bcl-2 inhibitors in combination with PBD-containing ADCs, AML cell lines were plated in 384-well tissue culture dishes and treated with antibody drug conjugates (ADCs) alone, Bcl-2 inhibitors alone, or combinations of ADCs with ABT-199 or ABT-263 for 96 hours at 37° C. For assessment of hypomethylating agents (HMAs) in combination with PBD-containing ADCs, AML cell lines were plated in 384-well tissue culture dishes and primed for 4 consecutive days with 5-azacytidine (vidaza/azacitidine) or 5-aza-2-deoxycytidine (decitabine). 24 hours after the last priming treatments with HMAs, cells were treated with ADCs alone, HMAs alone, or combinations of ADCs with 5-azacytidine or 5-aza-2-deoxycytidine for 96 hours at 37° C. Cell viability for the cell lines was measured using CelltiterGlo (Promega Corporation, Madison, Wis.) according to the manufacturer's instructions. To measure viability, cells were incubated for 25 minutes at room temperature with the CellTiter-Glo reagents and luminescence was measured on an Envision plate reader (Perkin Elmer, Waltham, Mass.).

Drug Combination Computational Analysis

Data Organization and Normalization: For the purpose of downstream analyses, CellTiter-Glo luminescence values are converted to viability percentages as follows. Luminescence values are arranged in a matrix with the i,jth entry, $V(i,j)$, $i=1, \ldots, N$, $j=1, \ldots, M$, representing cell viability after treating with Drug 1 at concentration i and Drug 2 at concentration j. Concentrations are assumed to increase with i and j, with $i=1$ corresponding to no treatment with Drug 1, and $j=1$ corresponding to no treatment with Drug 2. Different normalization schemes are possible, but for this analysis we simply divide the matrix of luminescence values by the $V(1,1)$ entry, which corresponds to no treatment with either drug. Normalization is performed at an individual replicate level. Additivity Models: In the realm of drug combination studies, the concepts of synergy and antagonism refer to cooperative or non-cooperative deviations from models of additivity, which under various assumptions reflect a null expectation of the effect of combining two agents on cell viability. Additivity models predict the combined effect given the separate single-agent effects. That is, given a combination dose (i0, j0) an additivity model $W(i0,j0)$ predicts $V(i0,j0)$ from $\{V(1,j), j=1, \ldots M\}$ and $\{V(i,1), i=1, \ldots N\}$, under the null expectation. Commonly used additivity models include Bliss, Loewe and Highest Single Agent (HSA) [1,2,3]. The Loewe model requires continuous and monotone single-agent data, for which we use a Hill equation, $$F(x) = (U_\infty - U_0)\left(\frac{x^H}{x^H + Ec50^H}\right) + U_0$$

where $U_\infty$, $U_0$, $H$, and Ec50 are fitted parameters. A Hill equation is fit to each single-agent dataset: F1(x) is fit to $\{V(i,1)\}$, and F2(x) is fit to $\{V(1,j)\}$. Parameter fitting is performed using the method of non-linear least squares, as implemented in the R function nls( ). Bliss and HSA models can be calculated using either fitted or non-fitted single-agent data. In case multiple replicates are available at each dose, the Hill equations are fit simultaneously to all data points. In models using non-fitted data, the median observation at each single-agent dose is used to compute the model. Statistical determination of synergy/antagonism: Given an additivity model $W(i,j)$ and observed data $V(i,j)$, the dose combination (i,j) is deemed to be synergistic if $V(i,j)<W(i,j)$ (greater cytotoxicity than predicted under the combined treatment), and antagonistic if $V(i,j)>W(i,j)$. If multiple replicates $V(i,j,k)$, $k=1, \ldots K$, exist for each $V(i,j)$, one-sided t-tests can be used to assign a p-value to test the specific combination (i,j) for synergy ($\{V(i,j,k)-W(i,j)<0$, $k=1, \ldots K\}$) or antagonism ($\{V(i,j,k)-W(i,j)>0, k=1, \ldots K\}$). In testing all possible M*N dose combinations, we adjust for multiple testing using a Bonferroni correction. To further adjust for the potential occurrence of outlier measurements, and to highlight the assumption that if a dose combination (i,j) is truly synergistic, then neighboring dose combinations are likely to be synergistic, we introduce the concept of combination block tests. In this case, for a fixed combination (i0,j0), we consider the 3×3 block of nine combinations $\{V(i0+i, j0+j); i=0, 1, 2; 1=0, 1, 2\}$, and ask if they collectively trend greater or less than the model predictions $\{W(i0+i, j0+j); i=0, 1, 2; j=0, 1, 2\}$. This translates in a straightforward way to a combination block t-test for synergy by testing $\{V(i0+i,j0+j)-W(i0+i,j0+j)<0; i=0, 1, 2; j=0, 1, 2\}$; or in the case of multiple replicates, $\{V(i0+i,j0+j,k)-W(i0+i,j0+j)<0; i=0, 1, 2; j=0, 1, 2; k=1, \ldots K\}$. The block t-test for antagonism uses the reverse inequality. We test over all 3×3 blocks, and adjust the p-values accordingly using a Bonferroni correction. Synergy metrics: best dose combinations and PTCDS: A number of synergy metrics are considered, in turn emphasizing strongly synergistic individual dose combinations or synergy across a range of combinations. Best dose combination: For a given experiment, the "best dose" combination is defined by scanning all 3×3 combination blocks that are tested as significantly synergistic at p<0.01, using the combination block test described above, for the single dose combination (i0, j0) that gives the greatest absolute positive difference $W(i0,j0)-V(i0,j0)$ between the additive model and the observed data. The metric recorded is this difference. In the case of multiple replicates we use the median of the observations, $\overline{V}(i0,j0)=\text{median}\{V(i0,j0, k), k=1, \ldots K\}$, to represent the observed data at a fixed combination. Number of synergistic combination blocks: This is simply the number of (possibly overlapping) 3×3 dose combination blocks that tested as significantly synergistic at p<0.01 using the combination block test described above. Percent Total Cytotoxicity Due to Synergy (PTCDS): The cytotoxicity achieved at dose combination (i,j) is simply the value $100-V(i,j)$ (more generally, we replace 100 by the maximum value of the additivity model $W_m=\max\{W(i,j), i=1, \ldots N, j=1, \ldots, M\}$). The total cytotoxicity observed across all dose combinations can therefore be defined as $$TC=\Sigma\{W_m-V(i,j), i=1, \ldots, N, j=1, \ldots, M\}.$$

On the other hand, $$TS=\Sigma\{W(i,j)-V(i,j), i=1, \ldots, N, j=1, \ldots, M\}$$

can be interpreted as the total synergy observed across all dose combinations, and TS/TC can be interpreted as the proportion of total cytotoxicity due to synergy. We define the Percent of Total Cytotoxicity Due to Synergy (PTCDS) as PTCDS=100*TS/TC. In the presence of multiple replicates, $V(i,j)$ is replaced in the above definitions by the median observation $V(i,j)$.

1, M. C. Berenbaum, What is synergy?, Pharmacol Rev. 41 (1989), pp. 93-141
2. S. Loewe, The problem of synergism and antagonism of combined drugs, Arzneimittelforschung, 3 (1953), pp. 285-290.
3. C. I. Bliss, The toxicity of poisons applied jointly, Ann Appl Biol, 26 (1939), pp. 585-615.

Results

In Vitro Anti-Tumor Activity of CD33-ADC, CD123-ADC, or CD19-ADC in Combination with Bcl-2 Inhibitors The cytotoxic activity of the CD33-ADC (h2H12EC antibody conjugated to SGD-1910, the pyrrolobenzodiazepine dimer drug-linker) was evaluated alone and in combination with hypomethylating agents or Bcl-2 inhibitors in several AML cell lines. As shown in FIG. 1, there was significant synergism in the cytotoxic activity of the ADC when combined with either 5-azacytidine (vidaza) or 5-aza-2-deoxycytidine (decitabine). However, the synergism exhibited by the combination of the CD33-ADC in combination with either ABT-199 or ABT 263 was even more striking.

The cytotoxic activity of the CD123-ADC (h7G3EC antibody conjugated to SGD-1910, the pyrrolobenzodiazepine dimer drug-linker) was evaluated alone and in combination with hypomethylating agents or Bcl-2 inhibitors in several AML cell lines. As shown in FIG. 1, there was significant synergism in the cytotoxic activity of the ADC when combined with either 5-azacytidine (vidaza) or 5-aza-2-deoxycytidine (decitabine). However, the synergism exhibited by the combination of the CD123-ADC in combination with either ABT-199 or ABT 263 was even more striking.

Figure 2:
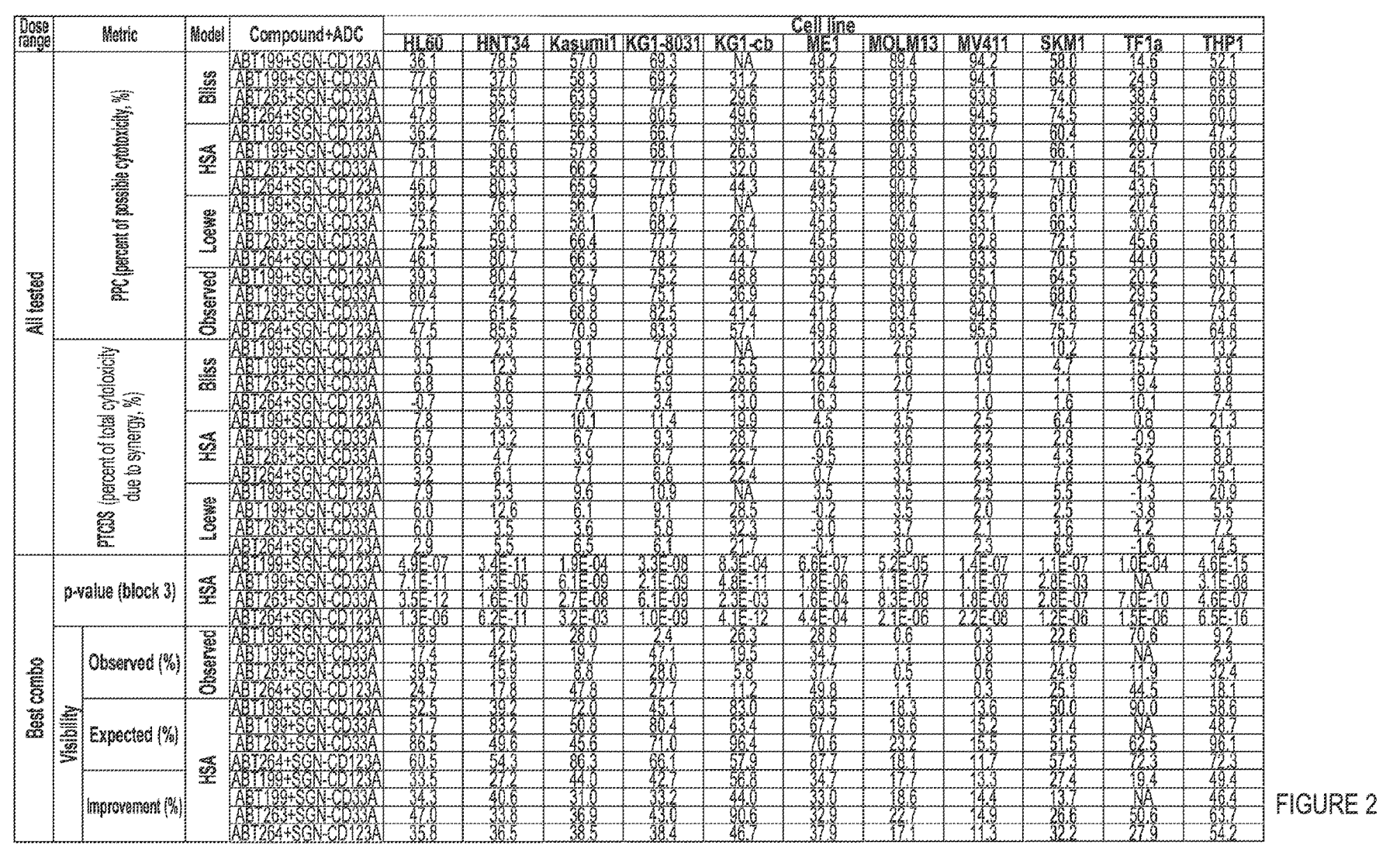

FIGS. 2 and 3 provide examples of the data and analysis used to identify synergistic drug combinations. The tested combinations were classified as synergistic if they exceeded the following cutoffs for the corresponding 3 HSA metrics in multiple cell lines: 15 synergistic 3×3 dose blocks with p-values less than 0.01, 20% activity improvement at the best dose, and PTCDS of 2%. As summarized in the accompanying table, this classification method concluded that SGN-CD33A+ABT-199, SGN-CD33A+ABT-263, SGN-CD123A+ABT-199, and SGN-CD123A+ABT-263 are synergistic combinations.

Figures 4A, 4B, 4C, 4D:
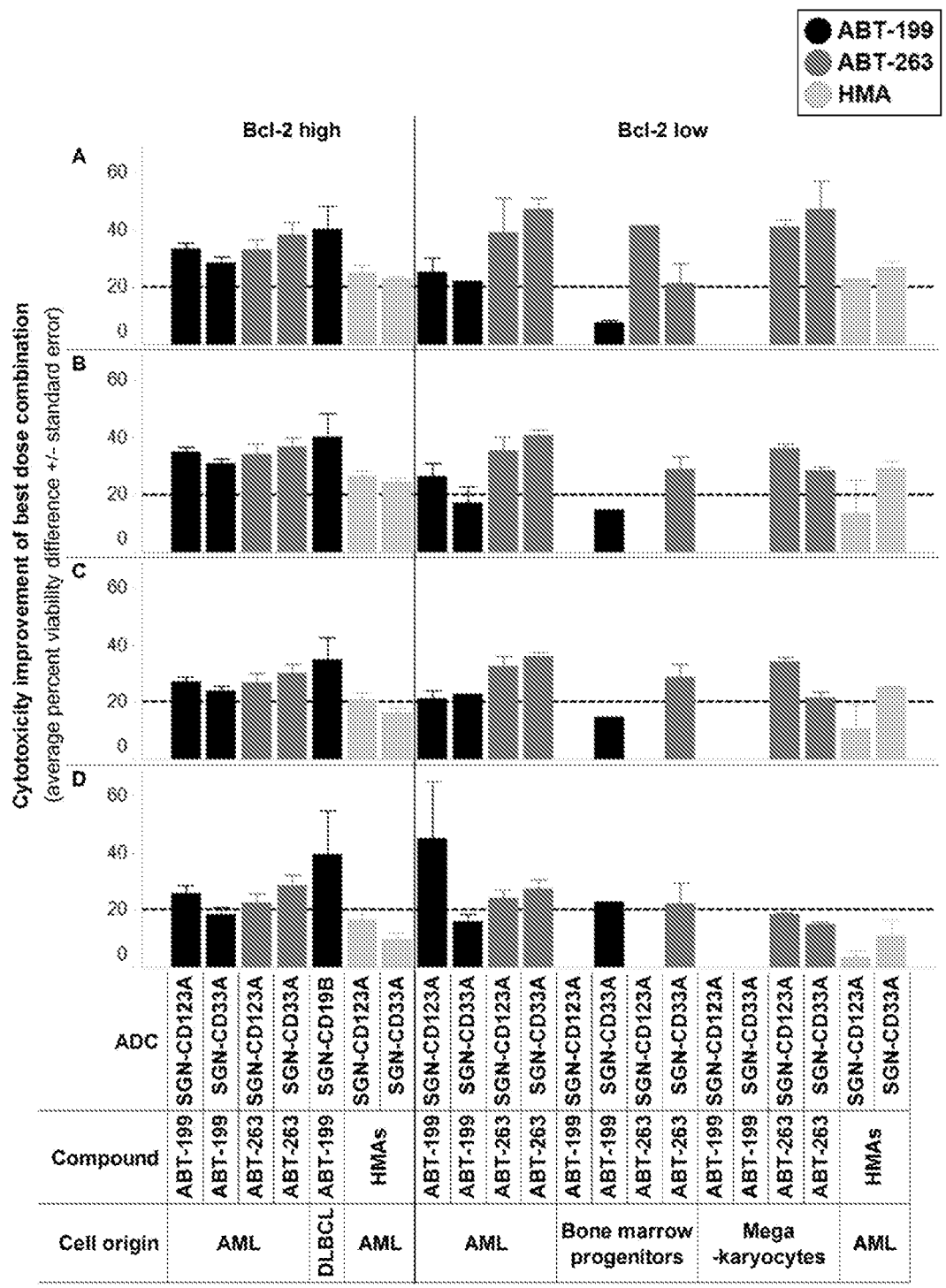
FIG. 4a-d provides cytotoxic improvement of best dose combination data for combinations of PBD-ADCs and Bcl-2 inhibitors ABT-199 or ABT-263 or for combinations of PBD-ADCs and hypomethylating agents. CD33-ADCs and CD123-ADCs comprising PBDs were tested with various agents on AML cell lines or on bone marrow progenitor cells or on megakaryocytes. CD19-ADCs comprising PBDs were tested in DLBCL cell lines.
Figures 5A, 5B, 5C, 5D:
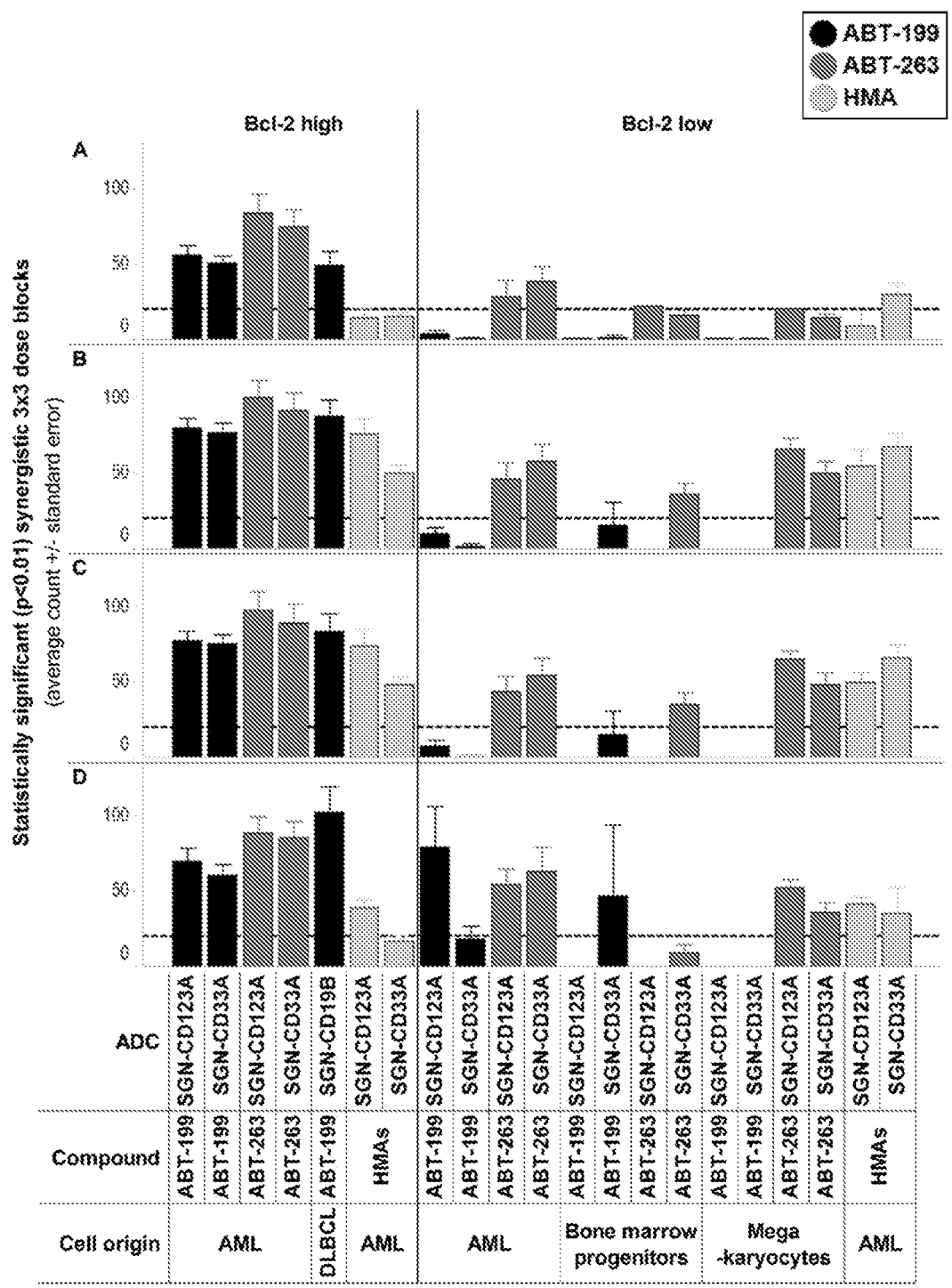
FIG. 5a-d provides statistically significant synergistic 3×3 dose block combination data for combinations of PBD-ADCs and Bcl-2 inhibitors ABT-199 or ABT-263 or for combinations of PBD-ADCs and hypomethylating agents. CD33-ADCs and CD123-ADCs comprising PBDs were tested with various agents on AML cell lines or on bone marrow progenitor cells or on megakaryocytes. CD19-ADCs comprising PBDs were tested in DLBCL cell lines.
Figures 6A, 6B, 6C, 6D:
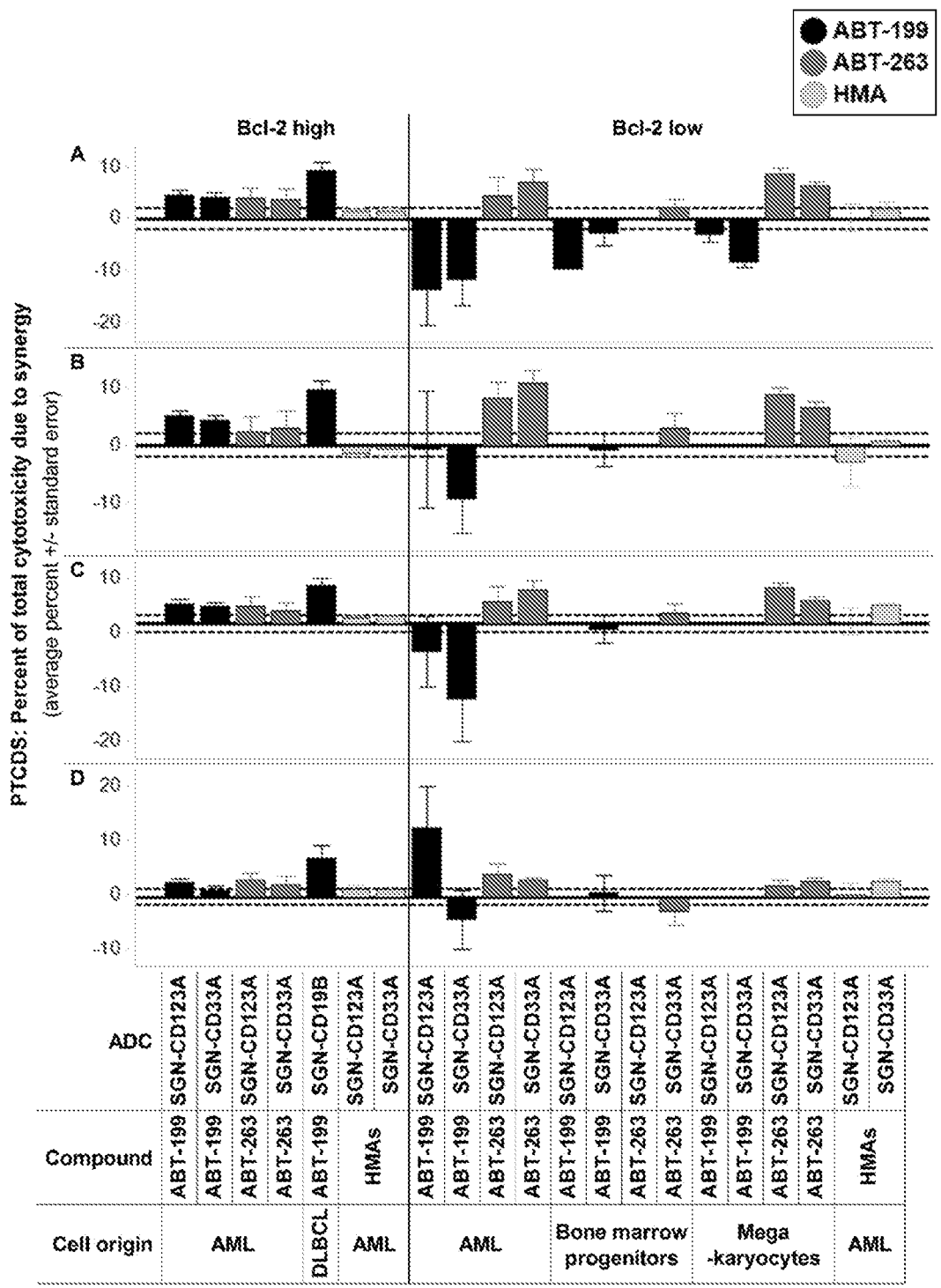
FIG. 6a-d provides percent of total cytotoxicity due to synergy combination data for combinations of PBD-ADCs and Bcl-2 inhibitors ABT-199 or ABT-263 or for combinations of PBD-ADCs and hypomethylating agents. CD33-ADCs and CD123-ADCs comprising PBDs were tested with various agents on AML cell lines or on bone marrow progenitor cells or on megakaryocytes. CD19-ADCs comprising PBDs were tested in DLBCL cell lines.
Figure 7:
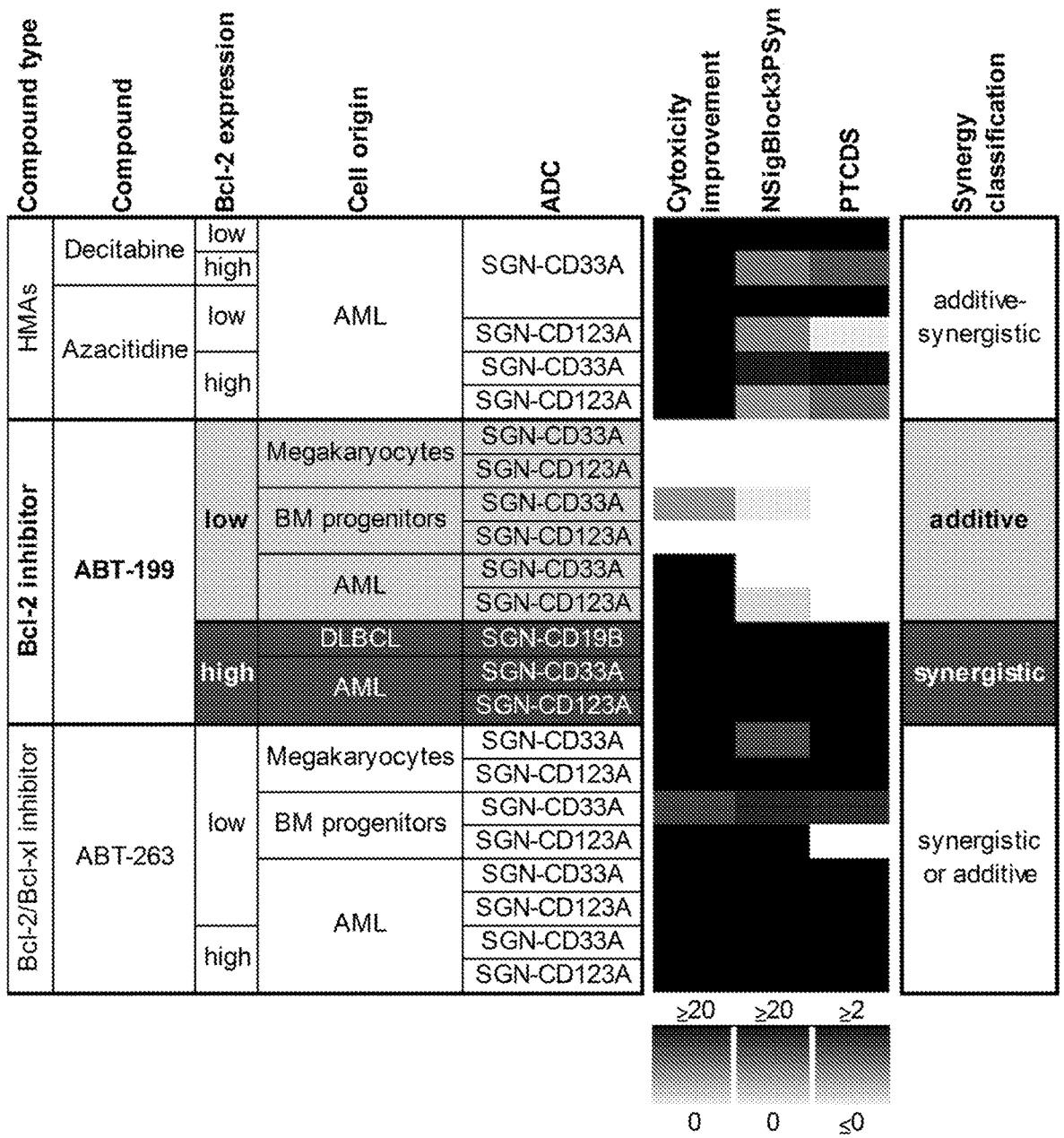
FIG. 7 provides a summary of synergy data for PBD-based ADCs in combination with hypomethylating agents (HMAs) or Bcl-2 inhibitors. Tested ADCs included a CD33-ADC, a CD123-ADC, and a CD19ADC. Cytotoxic improvement is the improvement of the best dose combination: % expected viability—observed viability. NSigBlock3PSyn is the number of statistically significant 3×3 dose blocks. PTCDS is the percent of total cytotoxicity due to synergy.

FIGS. 4-6 provide data for PBD-based ADCs in combination with hypomethylating agents (HMAs) or Bcl-2 inhibitors. Tested ADCs included a CD33-ADC (h2H12EC antibody conjugated to SGD-1910, the pyrrolobenzodiazepine dimer drug-linker), a CD123-ADC (h7G3EC antibody conjugated to SGD-1910, the pyrrolobenzodiazepine dimer drug-linker), and a CD19-ADC (hBU12EC antibody conjugated to SGD-1910, the pyrrolobenzodiazepine dimer drug-linker). Cytotoxic improvement is the improvement of the best dose combination: % expected viability—observed viability. NSigBlock3PSyn is the number of statistically significant 3×3 dose blocks. PTCDS is the percent of total cytotoxicity due to synergy. Synergy was tested in cell lines that expressed an antigen recognized by an ADC. Combinations with CD33 and CD123 ADCs were assessed in megakaryocytes, bone marrow (BM) progenitor cells, and a panel of AML cell lines expression CD33, CD123, or both. The tested AML cell lines included GDM1, HEL9217, HL60, HL60-RV, HNT-34, Kasumil, KG-1, ME-1, MOLM13, MV4-11, NOMO1, OCI-AML5, TFla, and THP-1. Combinations with CD19-ADCs were assessed in diffuse large B-cell lymphoma (DLBCL) cell lines that expressed CD19. CD19 positive cell lines included RC-K8, RI-1, RL, SU-DHL-4, U-2932, and WSU-DLCL2. The cell lines were also assessed for levels of Bcl-2 family levels by mRNA expression profiling or Western blotting. The data is summarized in FIG. 7.

The highest levels of synergy were seen in DLBCL cells and AML cells that expressed high levels of Bcl-2. Synergy was observed for the combination of ABT-199 and the CD19-ADC, ABT-199 and the CD33-ADC, and ABT-199 and the CD123-ADC. Lower, but still significant, synergy levels were seen in AML cells for the combination of ABT-263 and the CD33-ADC and the combination of ABT-263 and the CD123-ADC.

In Vivo Anti-Tumor Activity of CD33-ADC in Combination with Bcl-2 Inhibitors

FIG. 8 provides the results of a xenograft experiment using a vehicle control, ABT-199, a CD33-ADC comprising a PBD, or a combination of ABT-199 and a CD33-ADC comprising a PBD. Five million MOLM-13 cells were implanted subcutaneously in SCID mice. Tumor growth was monitored throughout the course of the study with bilateral vernier caliper measurements, and mean tumor volumes were calculated using the equation (0.5×[length×width$^2$]). When tumors reached approximately 100 mm$^3$, this marked day 1 of dosing and mice were randomly assigned into groups of 8 mice to receive ABT-199 formulation vehicle (vehicle), 100 mg/kg of ABT-199, a sub-optimal dose of the CD33-ADC SGN-CD33A (0.01 mg/kg), an optimal dose of SGN-CD33A (0.075 mg/kg), or a combination of 0.01 mg/kg of SGN-CD33A and 100 mg/kg of ABT-199. 24 hours prior to dosing, human immunoglobulin was administered intraveneously at 10 mg/kg of mouse body weight. ABT-199 formulation vehicle and ABT-199 were administered daily by oral gavage starting on day one of dosing for 14 days. SGN-CD33A was administered on day one of dosing. Mice with advanced tumor burden were sacrificed upon reaching tumor volumes of greater than 400 mm$^3$ or showing symptoms of hind limb paralysis, cranial swelling, and/or moribundity. As shown in FIG. 8, the mice that received the vehicle control and the mice that received ABT-199 alone had a 0% rate of survival by day 20. Mice that received an optimal dose of CD33-ADC or a combination consisting of sub-optimal doses of both ABT-199 and the CD33-ADC exhibited greater than 80% survival during the 40 day experiment. Mice that received a sub-optimal dose of the CD33-ADC alone exhibited increased survival relative to both vehicle and ABT-199 and decreased survival relative to both an optimal dose of CD33-ADC and a combination consisting of sub-optimal doses of both ABT-199 and the CD33-ADC. This result confirms the synergy observed in the in vitro experiments described above.

In Vivo Anti-Tumor Activity of CD19-ADC in Combination with Bcl-2 Inhibitors

Figure 9:
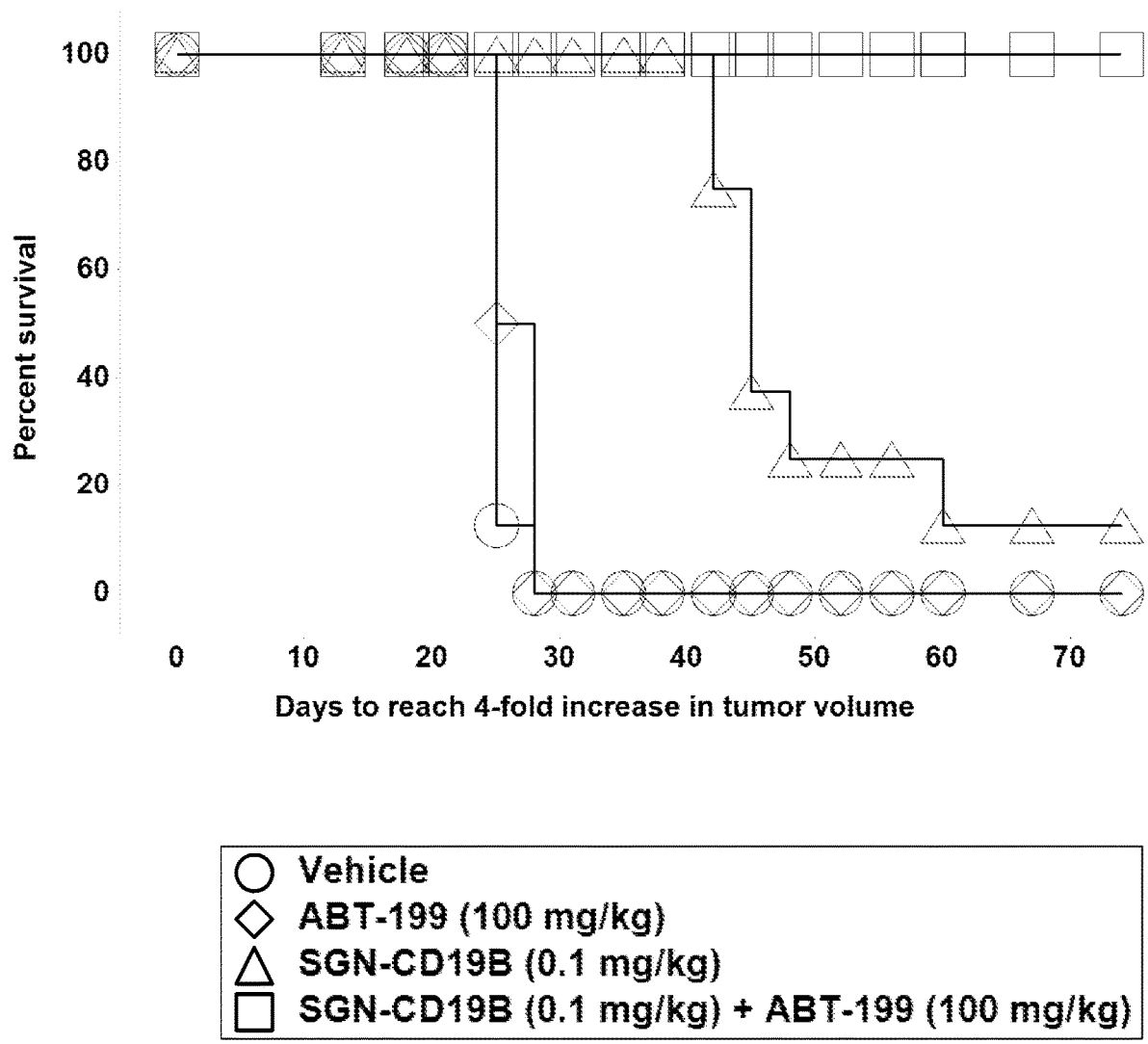
FIG. 9 provides the results of a xenograft experiment using a vehicle control, ABT-199, a CD19-ADC comprising a PBD, or a combination of ABT-199 and a CD19-ADC comprising a PBD.

FIG. 9 provides the results of a xenograft experiment using a vehicle control, ABT-199, a CD19-ADC comprising a PBD, or a combination of ABT-199 and a CD19-ADC comprising a PBD. The tested ADC was hBU12EC antibody conjugated to SGD-1910, the pyrrolobenzodiazepine dimer drug-linker. Five million RL cells were implanted subcutaneously in SCID mice. Tumor growth was monitored throughout the course of the study with bilateral vernier caliper measurements, and mean tumor volumes were calculated using the equation (0.5×[length×width$^2$]). When tumors reached approximately 100 mm$^3$, this marked day 1 of dosing and mice were randomly assigned into groups of 8 mice to receive ABT-199 formulation vehicle (vehicle), 100 mg/kg of ABT-199, a sub-optimal dose of the CD19-ADC (0.01 mg/kg), or a combination of 0.01 mg/kg of the CD19ADC and 100 mg/kg of ABT-199. 24 hours prior to dosing, human immunoglobulin was administered intraveneously at 10 mg/kg of mouse body weight. ABT-199 formulation vehicle and ABT-199 were administered daily by oral gavage starting on day one of dosing for 14 days. The CD19-ADC was administered on day one of dosing. Mice with advanced tumor burden were sacrificed upon reaching tumor volumes of greater than 400 mm$^3$ or showing symptoms of hind limb paralysis, cranial swelling, and/or moribundity. As shown in FIG. 9, the mice that received the vehicle control and the mice that received ABT-199 alone had a 0% rate of survival by day 30. Mice that received a combination consisting of sub-optimal doses of both ABT-199 and the CD19-ADC exhibited greater than 90% survival during the 40 day experiment. Mice that received a sub-optimal dose of the CD19-ADC alone exhibited increased survival relative to both vehicle and ABT-199 and decreased survival relative to the combination consisting of sub-optimal doses of both ABT-199 and the CD19-ADC. This result confirms the synergy observed in the in vitro experiments described below.

In Vitro Anti-Tumor Activity of CD19-ADC in Combination with Bcl-2 Inhibitors

Figures 10A, 10B, 10C:
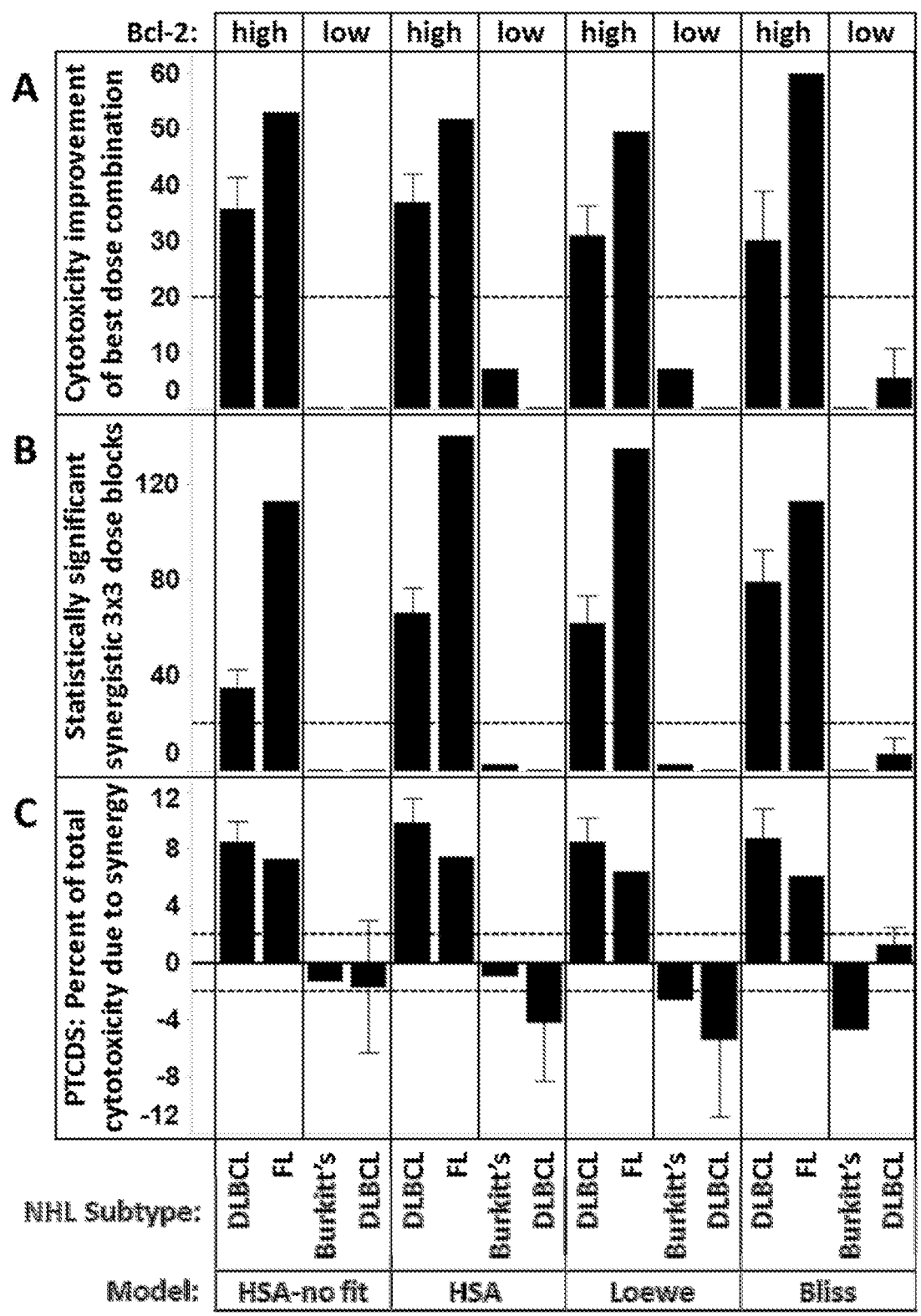
FIGS. 10a-10c provide cytotoxicity data for combination of a CD19-ADC comprising a PBD and ABT-199.

FIGS. 10a-10c provide data for PBD-based CD19ADCs in combination with the Bcl-2 inhibitor ABT-199. The tested ADC was hBU12EC antibody conjugated to SGD-1910, the pyrrolobenzodiazepine dimer drug-linker. Cytotoxic improvement is the improvement of the best dose combination: % expected viability—observed viability. NSigBlock3PSyn is the number of statistically significant 3×3 dose blocks. PTCDS is the percent of total cytotoxicity due to synergy. Synergy was tested in cell lines that expressed an antigen recognized by a CD19-ADC. Combinations with CD19 ADCs were assessed in the following cell lines: A4Fuk-NHL/DLBCL, BCL-2 low; DOHH2—NHL/FL, BCL-2 high; HT—NHL/DLBCL, BCL-2 low; Pfeiffer—NHL/DLBCL, BCL-2 high; Ramos—NHL/Burkitt's, BCL-2 low; RC-K8—NHL/DLBCL, BCL-2 high; RI-1—NHL/DLBCL, BCL-2 high; RL—NHL/DLBCL, BCL-2 high; SC-1—NHL/DLBCL, BCL-2 high; SU-DHL-16—NHL/DLBCL, BCL-2 high; SU-DHL-4 NHL/DLBCL, BCL-2 high; SU-DHL-6—NHL/DLBCL, BCL-2 high; SU-DHL-8—NHL/DLBCL, BCL-2 high; U-2932—NHL/DLBCL, BCL-2 high; WSU-DLCL2—NHL/DLBCL, BCL-2 high. The cell lines were also assessed for levels of Bcl-2 family levels by mRNA expression profiling or Western blotting. The combination of the CD19ADC and ABT-199 exhibited synergy in cells lines derived from multiple subtypes of NHL It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating cancer in a subject in need of such treatment, the method comprising administering an antibody drug conjugate (ADC) and a Bcl-2 inhibitor, wherein the ADC comprises an antibody conjugated to a PBD cytotoxic agent, wherein the Bcl-2 inhibitor is selected from the group consisting of ABT-199 and ABT-263, and wherein the antibody is selected from the group consisting of:
    a) an anti-CD33 antibody comprising the light chain variable region of SEQ ID NO: 1 and the heavy chain variable region of SEQ ID NO: 2; and
    b) and anti-CD19 antibody comprising the light chain variable region of SEQ ID NO: 10 and the heavy chain variable region of SEQ ID NO: 11.

2. The method of claim 1, wherein the PBD cytotoxic agent has the formula

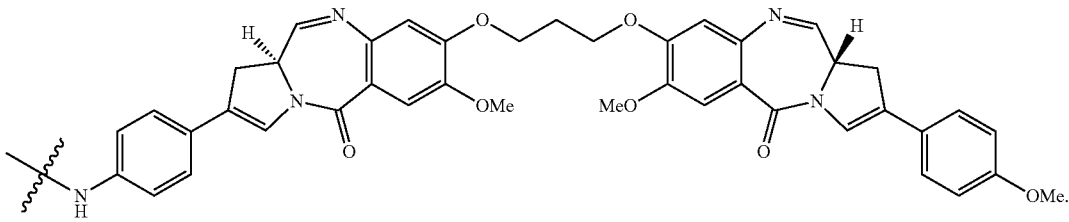 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

3. The method of claim 1, wherein the Bcl-2 inhibitor is ABT-199.

4. The method of claim 1, wherein the Bcl-2 inhibitor is ABT-263.

5. The method of claim 2, wherein the antibody is an anti-CD33 antibody comprising the light chain variable region of SEQ ID NO: 1 and the heavy chain variable region of SEQ ID NO: 2.

6. The method of claim 5, wherein the antibody is h2H12.

7. The method of claim 6, wherein the Bcl-2 inhibitor is ABT-199.

8. The method of claim 1, wherein the antibody is an anti-CD33 antibody comprising the light chain variable region of SEQ ID NO: 1 and the heavy chain variable region of SEQ ID NO: 2.

9. The method of claim 8, wherein the cancer is acute myeloid leukemia or myelodysplastic syndrome.

10. The method of claim 1, wherein the antibody is an anti-CD19 antibody comprising the light chain variable region of SEQ ID NO: 10 and the heavy chain variable region of SEQ ID NO: 11.

11. The method of claim 10, wherein the cancer is selected from the group consisting of non-hodgkins lymphoma, diffuse large B-cell lymphoma, acute lymphocytic leukemia, and chronic lymphocytic lymphoma.

* * * * *